United States Patent [19]
Madzak et al.

[11] Patent Number: 6,083,717
[45] Date of Patent: Jul. 4, 2000

[54] UPSTREAM ACTIVATOR SEQUENCES AND RECOMBINANT PROMOTER SEQUENCES FUNCTIONAL IN YARROWIA AND VECTORS CONTAINING THEM

[75] Inventors: Catherine Madzak, Villeneuve le Roi; Sylvie Blanchin-Roland, Maurepas; Claude Gaillardin, Versailles, all of France

[73] Assignees: Institut National de la Recherche Agronomique; Institut National Agronomique Paris- Grignon, both of Paris, France

[21] Appl. No.: 08/952,973

[22] PCT Filed: Jun. 6, 1996

[86] PCT No.: PCT/IB96/00562

§ 371 Date: Jan. 6, 1998

§ 102(e) Date: Jan. 6, 1998

[87] PCT Pub. No.: WO96/41889

PCT Pub. Date: Dec. 27, 1996

[30] Foreign Application Priority Data

Jun. 8, 1995 [EP] European Pat. Off. ............. 95401322

[51] Int. Cl.[7] .............. C12P 21/06; C12P 21/04; G01N 33/53; C12N 1/16

[52] U.S. Cl. .............. 435/69.1; 435/7.1; 435/69.9; 435/254.2

[58] Field of Search ................... 435/7.1, 69.1, 435/69.9, 254.2

[56] References Cited

FOREIGN PATENT DOCUMENTS

0220864A1 5/1987 European Pat. Off. .
220 864 6/1987 European Pat. Off. .

OTHER PUBLICATIONS

S. Blanchin–Roland et al., "Two upstream activation sequences control the expression . . . *Yarrowia lipolytica*", Mol. Cell. Bio. 14(1), 1994, 327–338.
C. Gaillardin et al., "Genetic engeineering in *Yarrowia lipolytica*", J. Bas. Micro., vol. 28, No. 3 pp. 161–174, 1988.
Davidow et al. J. of Bact. vol. 169, No. 1 pp. 4621–4629, 1987.
Heslot et al. Micro Appl. Food Biotech abstract 1 sheet, 1990.

*Primary Examiner*—Kenneth R. Horlick
*Assistant Examiner*—Jeffrey Siew
*Attorney, Agent, or Firm*—Foley & Lardner

[57] ABSTRACT

The invention concerns an upstream activating sequence (UAS) functional in Yarrowia consisting essentially of at least one copy of a selected sequence, and an recombinant promoter sequence comprising such an UAS. It concerns vectors comprising the recombinant promoter sequence and recombinant yeasts containing them, as well as process for producing a protein in yeast.

28 Claims, 20 Drawing Sheets

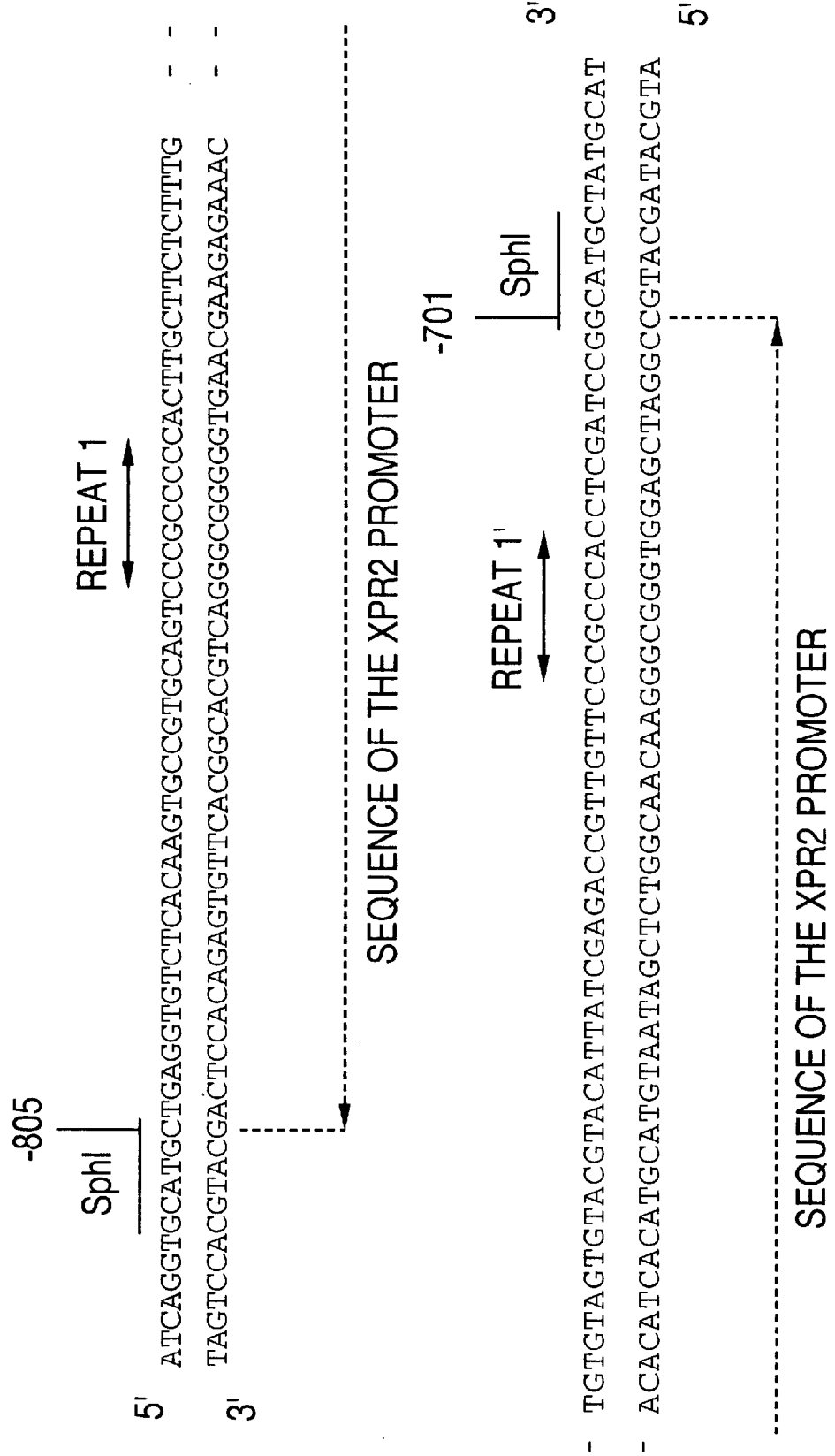

FIG. 3B

```
            -94
             |
GCATGC ACTGATCA CGGGCAAAAGTGCCGTATATATACAAGAGCCGTTTGCCAGCCACAGATT-
Sph I site   Bcl I site
                                             +1
                                              |
                                    TATATATACAA
-TTCACTCCACCACACCACCACATCACACACATACACCACACATCCACAATG GAA CCC GAA-
                                       |
                                      +18
-ACT AAG GATCC C GTC GTT TTA ..... lacZ......
         BamH I site  10  11  12
```

△ : "UASIB" FRAGMENT IN DIRECT ORIENTATION 6,083,717

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: double
      (D) TOPOLOGY: linear (ii) MOLECULE TYPE: DNA (xi) SEQUENCE DESCRIPTION: SEQ ID NO:1:

TGTCTCACAA GTGCCGTGCA GTCC                                         24

(2) INFORMATION FOR SEQ ID NO:2:

(i) SEQUENCE CHARACTERISTICS:
      (A) LENGTH: 8 base pairs
      (B) TYPE: nucleic acid
      (C) STRANDEDNESS: double
      (D) TOPOLOGY: linear (ii) MOLECULE TYPE: DNA (xi) SEQUENCE DESCRIPTION: SEQ ID NO:2:

TCCCGCCC                                                                       8

(2) INFORMATION FOR SEQ ID NO:3:

(i) SEQUENCE CHARACTERISTICS:
      (A) LENGTH: 78 base pairs
      (B) TYPE: nucleic acid
      (C) STRANDEDNESS: double
      (D) TOPOLOGY: linear (ii) MOLECULE TYPE: DNA (xi) SEQUENCE DESCRIPTION: SEQ ID NO:3:

TCCCGCCCCC ACTTGCTTCT CTTTGTGTGT AGTGTACGTA CATTATCGAG ACCGTTGTTC    60

CCGCCCACCT CGATCCGG                                               78

(2) INFORMATION FOR SEQ ID NO:4:

(i) SEQUENCE CHARACTERISTICS:
      (A) LENGTH: 105 base pairs
      (B) TYPE: nucleic acid
      (C) STRANDEDNESS: double
      (D) TOPOLOGY: linear (ii) MOLECULE TYPE: DNA (xi) SEQUENCE DESCRIPTION: SEQ ID NO:4:

CTGAGGTGTC TCACAAGTGC CGTGCAGTCC CGCCCCCACT TGCTTCTCTT TGTGTGTAGT    60

GTACGTACAT TATCGAGACC GTTGTTCCCG CCCACCTCGA TCCGG                105

(2) INFORMATION FOR SEQ ID NO:5:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:5:

ATCAGGTGCA TGCTGAGGTG TCTCACAAGT GC                32

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

ATGCATAGCA TGCCGGATCG AGGTGGGCGG                   30

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

TCTTGGGATC CTTAGTTTCG GGTTCCAT                     28

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GGTTTAGGCA TGCACTGATC ACGGGCAAAA GTGCGT            36

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

ACCATGTTTC AGCGCAATCC GACTTCCAAC CC                32

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

GCCAAACGTG ATCAGAAATG GTCACCCAGG AC                32

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

CGTCGTGATT AGCGCCG                                 17

(2) INFORMATION FOR SEQ ID NO:12:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

CAGTTTCTTG ATCATATGGT CACCAGAAAC ACGATATAAA CC      42

(2) INFORMATION FOR SEQ ID NO:13:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GCATCGTCTT GGCGCGTCTT GGCGAGAGCC GTGTTTCGTG ACGCAATG  48

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:14:

CCTGAGGTGT CTCACAAGTG CCGTGCAGTC CGCATG             36

(2) INFORMATION FOR SEQ ID NO:15:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:15:

CGGACTGCAC GGCACTTGTG AGACACCTCA GGCATG             36

(2) INFORMATION FOR SEQ ID NO:16:

(i) SEQUENCE CHARACTERISTICS:
        (A) LENGTH: 129 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:16:

```
ATCAGGTGCA TGCTGAGGTG TCTCACAAGT GCCGTGCAGT CCCGCCCCCA CTTGCTTCTC      60

TTTGTGTGTA GTGTACGTAC ATTATCGAGA CCGTTGTTCC CGCCCACCTC GATCCGGCAT     120

GCTATGCAT                                                             129
```

(2) INFORMATION FOR SEQ ID NO:17:

(i) SEQUENCE CHARACTERISTICS:
        (A) LENGTH: 139 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:17:

```
GCATGCACTG ATCACGGGCA AAAGTGCGTA TATATACAAG AGCGTTTGCC AGCCACAGAT      60

TTTCACTCCA CACACCACAT CACACATACA ACCACACACA TCCACAATGG AACCCGAAAC     120

TAAGGATCCC GTCGTTTTA                                                  139
```

(2) INFORMATION FOR SEQ ID NO:18:

(i) SEQUENCE CHARACTERISTICS:
        (A) LENGTH: 48 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:18:

```
CTTGTCCAGA AACACGATAT AAACCCCATC GACGGGCCCG TTGAAGAG                   48
```

(2) INFORMATION FOR SEQ ID NO:19:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:19:

```
TTCAACGGGC CGTCGATGG GGTGCATGCC GTGTTTCTGG AC                          42
```

(2) INFORMATION FOR SEQ ID NO:20:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

```
GCATGCACTG ATCAGAAATG GTCACCTGGA TGTATATAAG GAGGACTCAT AATGAAGTTC        60

GCTCTGGCCG TCGTT                                                        75

(2) INFORMATION FOR SEQ ID NO:21:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

GCATGCACTG ATCATATGGT CACCAGAAAC ACGATATAAA CCCACAATGG AATTCAAGGA        60

TCCCGTCGTT TTA                                                          73

(2) INFORMATION FOR SEQ ID NO:22:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

AGGCTCTCAA GGGCATCGGT CGACTGATCA ATACAACCAC ACACATCCAC AATGAAGCTC        60

GCTACCGCCT TTACTATTCT CACTGCACGG ATGGATCTGG CTTTCTCAAG CGAGCTGAGA       120

TCTGATCCAA CTAC                                                        134
```

UPSTREAM ACTIVATOR SEQUENCES AND RECOMBINANT PROMOTER SEQUENCES FUNCTIONAL IN YARROWIA AND VECTORS CONTAINING THEM

This application is a 371 of PCT/IB96/00562 filed Jun. 6, 1996 and claims priority to EPO 95401322.3 filed Jun. 8, 1995.

The present invention relates to a system allowing for improved protein expression in yeasts, more particularly in *Yarrowia lipolytica*. It relates to recombinant upstream activator sequences, promoter sequences and more specifically hybrid promoter sequences, functional in Yarrowia, and vectors containing them. Another object for the invention is a recombinant yeast transformed with such vectors, and a process for producing a protein in *Yarrowia lipolytica*.

*Yarrowia lipolytica* is a dimorphic yeast which can grow on a limited number of carbon sources, including glucose and glycerol, paraffines such as n-alkanes and alkenes (Klug and Markovetz, 1967 and 1969; Bassel and Mortimer, 1973), lipids and proteins (Ogrydziak et al., 1977) but not sucrose. To degrade proteins, depending on growth conditions, *Yarrowia lipolytica* secretes proteases (Ahearn et al., 1968, Kamada et al., 1972). For example, in alkaline or neutral medium, it secretes an Alkaline Extracellular Protease (AEP) (Tobe et al., 1976; Ogrydziak et al., 1977; Ogrydziak and Scharf, 1982). The corresponding gene, XPR2, has been cloned independently by Davidow et al. (1987), Matoba et al. (1988) and Nicaud et al. (1989).

Many eukaryotic promoters, especially yeast promoters, have now been extensively studied. It has been demonstrated that regulation of gene expression involves multiple interactions between transcription factors bound within a promoter. Multiple sites may be required for, and multiple proteins may be associated with, the functioning of even the smallest cis-acting elements. In yeast cells, upstream activation sequences ($UAS_S$) are necessary for transcription. They function in either orientation and at a variable distance with respect to the TATA box and transcription start site, but in contrast to enhancers in higher eukaryotes, they must be upstream from these basal elements. $UAS_S$ are targets for two types of trancriptional activators. The first class of activators, which includes HAP1 and ACE1, bind $UAS_S$ only under conditions of active transcription of the downstream gene. The second class is represented by ADR1, HSTF, PUT3, and GAL4; these proteins are permanently bound to $UAS_S$, but their activity is regulated.

Although most repression phenomena in yeast cells seem to result from inactivation or absence of transcription factors, some negative regulatory sites, or upstream repression sequences (URS), have also been identified.

The XPR2 gene from *Yarrowia lipolytica* encodes an inducible alkaline extracellular protease (AEP) which is the major protein secreted by this yeast (Davidow et al., 1987). The regulation of this gene is complex. Derepression of AEP occurs at pH above 6.0 on media lacking preferred carbon and nitrogen sources; full induction of the XPR2 promoter requires high levels of peptones in the culture medium, although the exact nature of the inducer is unknown. The functional XPR2 promoter encompasses roughly 900 bp.

EP 138 508 discloses a process for transformation of *Yarrowia lipolytica* by integration of DNA having a region homologous with chromosomal DNA and a genetic marker.

EP 220 864 discloses a vector for expression and secretion of heterologous proteins in *Yarrowia lipolytica*. The vector must comprise a promoter sequence of a *Yarrowia lipolytica* gene and the signal sequence of the XPR2 gene of *Yarrowia lipolytica* operably linked to a gene for a heterologous protein. The promoter sequence can be the XPR2 promoter sequence, ie the upstream untranscribed region in front of the signal sequence.

Surprisingly, the inventors have shown that hybrid promoters containing only parts of the XPR2 promoter sequence can be used to obtain expression of a protein in *Yarrowia lipolytica*.

Furthermore, they have shown that hybrid promoters composed of tandem repeats of only a part of the XPR2 promoter sequence will allow the strong quasi-constitutive expression of a protein under its control, irrespective of the presence of peptones in the medium. These hybrid promoters are no longer repressed by the preferred carbon or nitrogen sources, nor by acidic conditions (pH lower than 6.0).

This represents a major industrial advantage for the production of secreted heterologous proteins since conventional medium can be used, at lower price. The further purification steps for the recovery of the desired protein will also be easier, since the high level of peptones (which are required for full induction of wild type XPR2 promoter and considerably complicate purification of secreted heterologous proteins) is no longer required.

A previous analysis of the XPR2 promoter (Blanchin-Roland et al., 1994) had identified two regions implicated in the activation of the expression ($UAS_S$): one distal (UAS1 from nucleotide −800 to −767 and −717 to −708) and another proximal (UAS2 from nucleotide −146 to −105). According to these former results, obtained by a deletion analysis, both UASs appeared to play equivalent roles regarding the regulation of XPR2 expression. Each UAS was able, in the absence of the other, to drive a regulation similar to that of the whole XPR2 promoter (namely, sensitivity to peptones and repression by the preferred carbon and nitrogen sources).

Surprisingly, it has now been found that the distal region (UAS1) of the XPR2 promoter can exhibit a physiological activity outside the XPR2 context, when placed upstream of the TATA region of another promoter. This UAS activity can be attributed to a sequence (SEQ ID NO: 1 in the DNA fragment termed "UAS1A") that was previously found protected in DMS footprinting in vivo experiments (Blanchin-Roland et al., 1994, and FIG. 1). The UAS effect was enhanced by the addition to these sequences of a neighbouring region containing two repeats of a sequence also previously found protected in footprinting experiments (SEQ ID NO: 2). The entire DNA fragment is termed "UAS1B". No repression was observed under conditions of culture that were repressive for the wild type XPR2 promoter (preferred carbon and nitrogen sources): the expression of the reporter protein under control of the hybrid promoter was enhanced in the inducing, basal and repressing media.

The analysis of the proximal UAS region (UAS2) has shown that a decamer sequence, tandemly repeated and protected in footprinting experiments (Blanchin-Roland et al., 1994, and FIG. 1), was able to mediate a decrease in the expression level under repressing conditions: this sequence exhibits the properties of an URS (upstream repressing sequence) sensitive to carbon and/or nitrogen sources.

Unexpectedly, this sequence was also, together with an adjacent sequence, partly protected in footprinting experiments (cf FIG. 1), necessary to the UAS activity.

The UAS2 therefore contains both activating and repressing elements. It appears, in striking contrast to the constitutive properties of the UAS1, to have conserved at least some of the regulation of the whole XPR2 promoter.

Accordingly, the present invention provides upstream activating sequences, functional in Yarrowia, that escape the complex regulation of the wild type XPR2 promoter. They consist essentially of the sequences bounded by the nucleotides −805 and −701 of the sequence of the UAS1 region of the XPR2 promoter or of functional fragments thereof, which can be present in several copies. They must also be substantially devoid of the decameric repeat from UAS2 region, bounded by nucleotides −146 to −127 of the XPR2 promoter sequence.

More particularly, the present invention provides upstream activating sequences, functional in Yarrowia, consisting essentially of at least one copy of at least one sequence selected from:

a) SEQ ID NO: 1 or a sequence possessing at least 80% identity to SEQ ID NO: 1.

b)
  i) SEQ ID NO: 1 or a sequence possessing at least 80% identity and
  ii) at least one copy of SEQ ID NO: 2, or a sequence possessing at least 80% identity to SEQ ID NO: 2.

The position of the said sequences in the XPR2 promoter is shown in the FIGS. 1 and 2.

By "consisting essentially of", it must be understood that the UAS can also comprise restriction sites and other elements necessary for the construction and the ligation of the fragments.

The copies of the above-identified fragments which are present in the UAS according to the invention can be either tandem repeats (all direct or all inverted) or any combination of both orientations.

According to one embodiment of the invention, the UAS is consisting essentially of b')
  i) at least one copy of the SEQ ID NO: 1 or a sequence possessing at least 80% identity, and
  ii) at least one copy of a neighbouring sequence, that contains two repeats corresponding to the SEQ ID NO: 2 (as shown in the FIG. 1, it could exist a partial overlapping between the SEQ ID NO: 1 and one of the SEQ ID NO: 2).

More particularly, the UAS can consist essentially of:

c)
  i) at least one copy of SEQ ID NO: 1 or a sequence possessing at least 80% identity, and
  ii) at least one copy of SEQ ID NO: 3 or a sequence possessing at least 80% identity.

SEQ ID NO: 3 corresponds to a region of the XPR2 promoter containing two repeats of SEQ ID NO: 2. As shown in the FIG. 1, it could exist as a partial overlap between the SEQ ID NO: 1 and the SEQ ID NO: 3.

A preferred UAS according to the invention is consisting essentially of at least one copy of:

d) SEQ ID NO: 4 or a sequence possessing at least 80% identity to SEQ ID NO: 4.

The SEQ ID NO: 4 corresponds to the XPR2 promoter sequence bounded by the nucleotides −805 to −701, present in the large "UAS1B" fragment, as shown in FIGS. 1 and 2.

The invention also encompasses variants of the claimed sequences which retain the physiological activity, as they can be determined by the man skilled in the art.

When several copies of "UAS1B" were inserted in tandem, the expression increased: the effect was more than additive with a second copy, suggesting a synergic interaction, and became only additive for each new added copy. The level of expression obtained with four copies is very high in the three media, of the same order of magnitude as that for the native XPR2 promoter under inducing conditions. The hybrid promoters obtained do not require the addition of peptones and are no longer repressed by the carbon and nitrogen sources, nor by acidic conditions of culture. These strong quasi-constitutive promoters are particularly useful for the production of heterologous proteins.

In the UAS according to the invention, the number of copies of said sequences respectively a), b), c) or d) is in the range of 1 to 8, the number of copies of SEQ ID NO: 2 being in the range of 0 to 16. The sequences can be either in the same orientation or not.

The UAS according to the invention can consist notably of two tandem copies of said sequences a), b), c) or d), or of four tandem copies of said sequences a), b), c) or d).

The invention is also relating to a recombinant promoter sequence which is functional in yeasts and comprises an UAS as described above. Such recombinant promoters are particularly useful for Yarrowia yeasts, preferably *Yarrowia lipolytica*.

Promoter sequences according to the invention will comprise one or more copies of "UAS1B", or its derivatives. With four tandem copies of "UAS1B", they control the quasi-constitutive expression of a gene, in non-inducing medium, at the same level as the expression obtained in an inducing medium with the wild type XPR2 promoter. They allow the use of acidic conditions of culture, of culture media containing preferred carbon and/or nitrogen sources and avoid the addition of peptones in the medium.

The recombinant promoter sequence will further comprise a TATA box. The TATA box is preferably that of a *Yarrowia lipolytica* gene; the TATA box can be that of a gene differing from the XPR2 gene, for example the TATA box of the LEU2 promoter.

Another object of the invention is a vector for the expression of a protein in yeast, comprising a recombinant promoter sequence as defined before, operably linked to a gene of interest. The gene of interest is encoding a protein, which in one embodiment is an heterologous protein of the yeast. Gene encoding homologous protein of the yeast are also comprised in the vectors of the invention. The vectors of the invention are particularly adapted for *Yarrowia lipolytica*.

In one embodiment of the invention the vector is furthermore comprising sequences allowing its insertion into the chromosome. These sequences are particular sequences presenting homology with sequences of the chromosome of the yeast, thus allowing recombination and integration; such elements will be determined by the man skilled in the art (as described in EP 138 508).

Several copies of the vector can therefore be inserted in the chromosome of the Yarrowia yeast.

In another embodiment of the invention, the vector is of auto-replicating type, and is furthermore comprising replicating sequences. Such sequences have been disclosed for example in the European patent application number 89 400218.7.

The invention is also comprising recombinant yeast transformed with a vector according to the invention, particularly of *Yarrowia lipolytica* species.

In one aspect of the invention the recombinant promoter sequence operably linked to the gene of interest is integrated into the chromosome of the yeast, in at least one copy.

In another aspect the vector is present in the yeast as an autonomously replicating vector.

Finally, the invention is also relating to a process for producing a protein in *Yarrowia lipolytica*, comprising the step of culturing recombinant *Yarrowia lipolytica* cells transformed with a vector as defined here-above.

The protein can be a homologous or a heterologous protein of Yarrowia.

The construction can further comprise elements allowing the secretion of the protein.

Otherwise, the recombinant yeast can be used intact, for example as food additive. The protein of interest could also be recovered by disrupting the yeast and further purifying the extract.

In particular, the invention is comprising a process for producing an heterologous protein comprising the steps of:
i) introducing into a *Yarrowia lipolytica* a vector comprising recombinant UAS operably linked to the gene encoding the said protein,
ii) culturing said *Yarrowia lipolytica* obtained in i) in a medium substantially devoid of peptones,
iii) recovering said heterologous protein.

Finally, the invention is relating to a process for enhancing the expression of a protein in *Yarrowia lipolytica*, comprising the step of introducing in said *Yarrowia lipolytica* a recombinant promoter sequence comprising one or more copies of at least one sequence selected from:
a) SEQ ID NO: 1 or a sequence possessing at least 80% identity to SEQ ID NO: 1.
b)
   i) SEQ ID NO: 1 or a sequence possessing at least 80% identity and
   ii) at least one copy of SEQ ID NO: 2, or a sequence possessing at least 80% identity to SEQ ID NO: 2.
c)
   i) SEQ ID NO: 1 or a sequence possessing at least 80% identity and
   ii) at least one copy of SEQ ID NO: 3, or a sequence possessing at least 80% identity to SEQ ID NO: 3.
d) SEQ ID NO: 4 or a sequence possessing at least 80% identity to SEQ ID NO: 4.

The following strains of *E. coli* and of *Y. lipolytica* have been deposited at the "Collection Nationale de Cultures de Microorganismes" of the Institut Pasteur in Paris (France):
   *E. coli* strain HB101 containing plasmid pINA354: Accession Number I-1579
   *E. coli* strain HB101 containing plasmid pINA404: Accession Number I-1580
   *Y. lipolytica* strain JM23SB: Accession Number I-1581

The invention will be further understood with the following examples, which are not in any way intended to limit its scope.

In these examples, it will be referred to the Figures:

The two regions of the distal UAS1 and the proximal UAS2 are schematized. The sequences found protected during DMS footprinting in vivo experiments (Blanchin-Roland et al., 1994) are underlined with bold lines (this method concerns only the GC base pairs). The repeated sequences are underlined with arrows. The DNA fragments used in the construction of the hybrid promoters (data for UAS1 region shown in Examples 3 and 4, data for UAS2 region not shown) are indicated. The revendicated sequences (SEQ ID NOS 1 to 4) are also indicated.

Figure 2A:
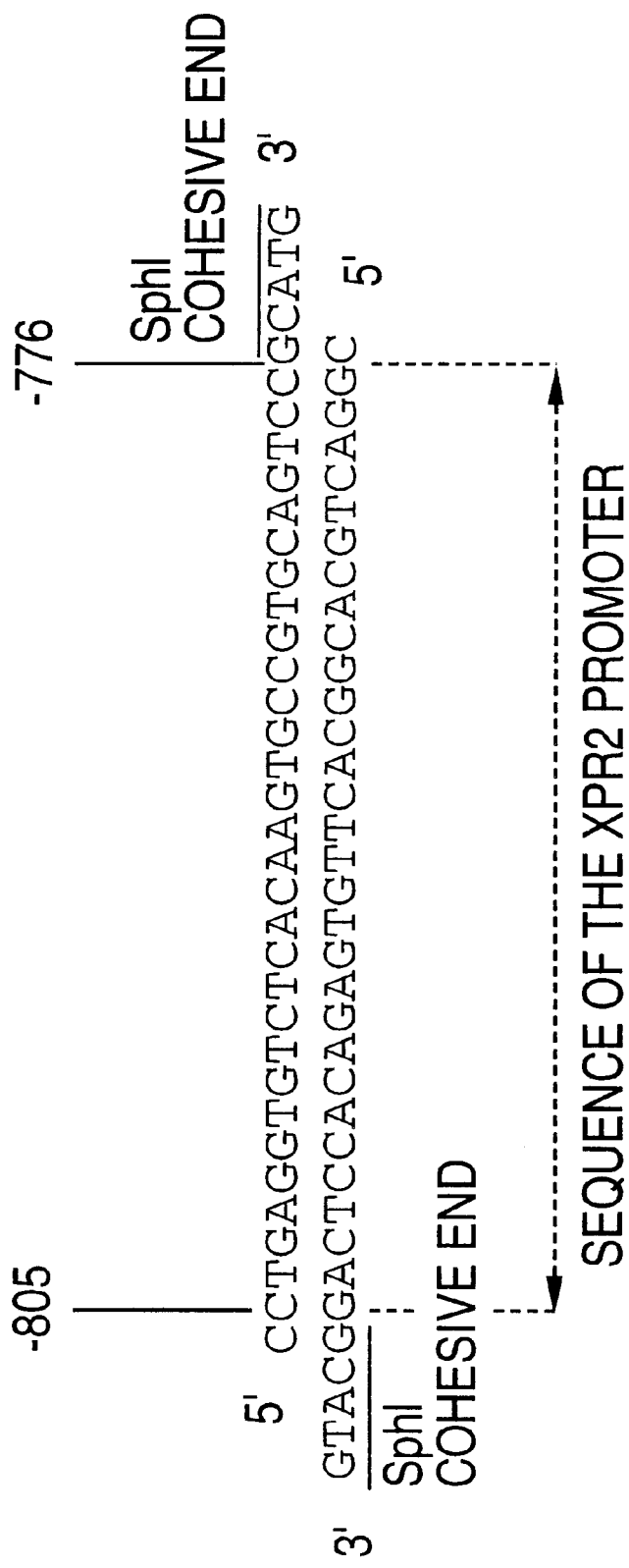

FIGS. 2A & 2B (SEQ ID NOS 14, 15 & 16, respectively): Sequence of the DNA fragments, from the UAS1 region of the XPR2 promoter, used in the hybrid promoters.

A/ sequence of the "UAS1A" fragment. "UAS1A" was obtained by hybridization of the two synthetic oligonucleotides shown. It consists essentially of the sequence bounded by the nucleotides −805 and −776 of the sequence of the XPR2 promoter, and carries cohesive ends for the SphI restriction enzyme, allowing its insertion at the SphI site of pINA781, upstream of the minimal LEU2 promoter (see FIG. 3), in both orientations and with different copy number.

B/ sequence of the "UAS1B" fragment. "UAS1B" consists essentially of the sequence bounded by the nucleotides −805 and −701 of the sequence of the XPR2 promoter. It was obtained by a PCR reaction using the plasmid pINA354 (see FIG. 4) as a template and the following mutagenic oligonucleotides (SEQ ID NOS 5 & 6, respectively):

oligo "UAS1B-L": 5' ATCAGGT GCATGCTGAGGTGTCTCACAAGTGC 3'
oligo "UAS1B-R": 5' ATGCATA GCATGCCGGATCGAGGTGGGCGG 3'

The mutations introduced to create new SphI restriction sites (underlined) are indicated in bold types. Following SphI digest, "UAS1B" can be inserted at the SphI site of pINA781, upstream of the minimal LEU2 promoter (see FIG. 3), in both orientations and with different copy number.

Figure 3A:
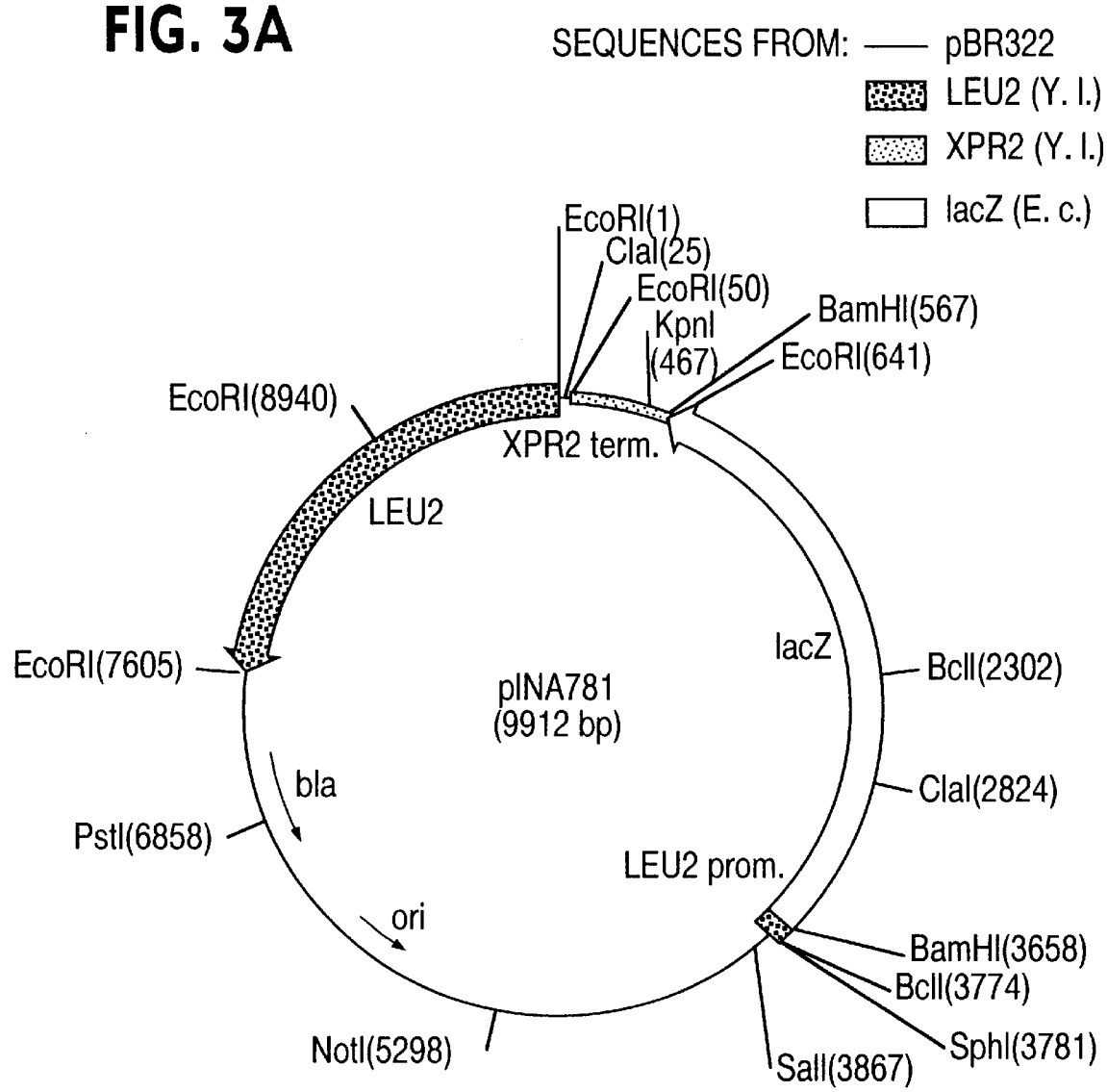

FIGS. 3A–3B (SEQ ID NO: 17): Map of the reporter pINA781 integrative plasmid.

Figure 4A:
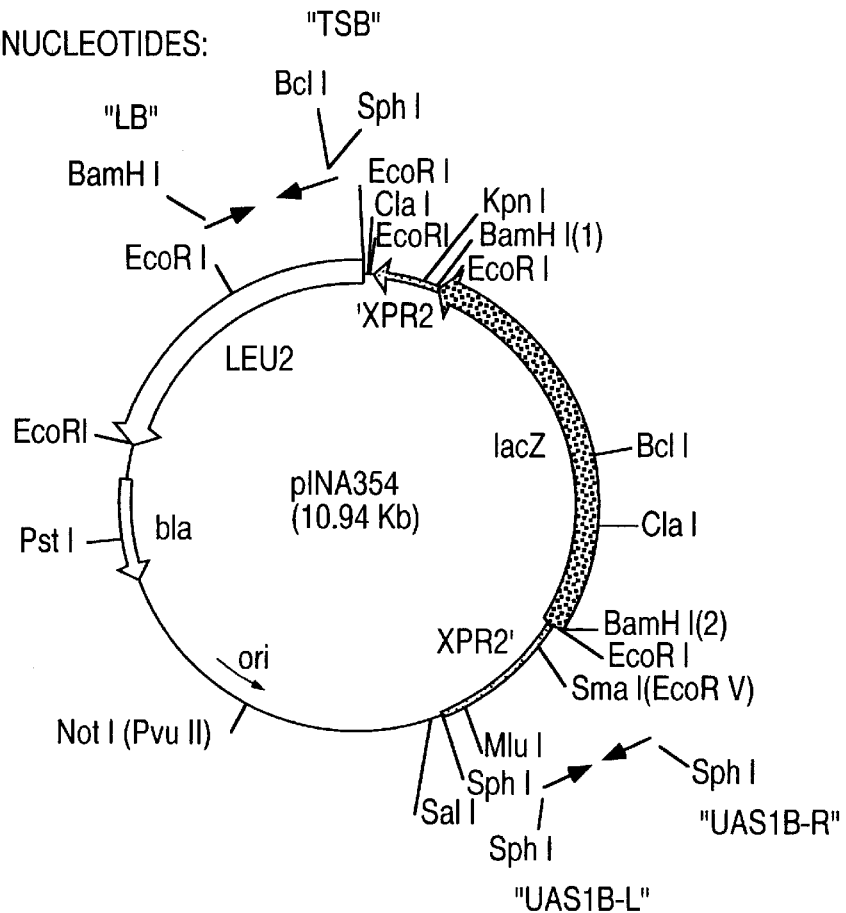

A/ map of pINA781. pINA781 was derived from the previously described pINA354 plasmid (Blanchin-Roland et al., 1994) shown in FIG. 4A.

The *E. coli* strain HB101 containing plasmid pINA354 (HB101[pINA354]) has been deposited at the "Collection Nationale de Cultures de Microorganismes" of the Institut Pasteur in Paris (France) under Accession Number I-1579.

A DNA fragment carrying the minimal LEU2 promoter region (determined from Gaillardin and Ribet, 1987) was obtained by a PCR reaction using pINA354 as a template and the two mutagenic oligonucleotides shown below (see also FIG. 4) (SEQ ID NOS 7 & 8, respectively):

oligo "LB": 5' TCTTGGGGATCCTTAGTTTCGGGTTCCAT 3'
oligo "TSB": 5' GGTTTAGGCATGCAC TGATCACGGGCAAAAGTGCGT 3'

The mutations introduced to create new restriction sites (underlined), respectively for BamHI, SphI and BclI, are indicated in bold types.

The PCR fragment carrying the minimal LEU2 promoter was digested with SphI and BamHI and was introduced into a pINA354 plasmid deleted of its own SphI-BamHI(2) fragment carrying the XPR2 promoter (see FIG. 4). In the resulting pINA781 plasmid, the minimal LEU2 promoter is able to direct the expression of the lacZ gene, due to the translational fusion realized at the BamHI(2) site, as shown below in B/. The unique SphI restriction site was used to introduce various DNA fragments from the XPR2 promoter. The unique NotI restriction site was used to direct the integration of the plasmids obtained into the genome of the *Y. lipolytica* JM23SB strain (Blanchin-Roland et al., 1994), at the pBR322 platform.

B/ fragment of sequence from pINA781 showing the minimal LEU2 promoter and the translational fusion with the lacZ reporter gene. The sequence conserved from the LEU2 promoter is bounded by the nucleotides −94 to +18 (in the numeration of the LEU2 gene). The TATA box and the ATG sequence are underlined in bold (Gaillardin and Ribet, 1987). GTC is the first conserved codon from the β-galactosidase sequence and corresponds to the tenth codon of the lacZ gene.

Figure 4B:
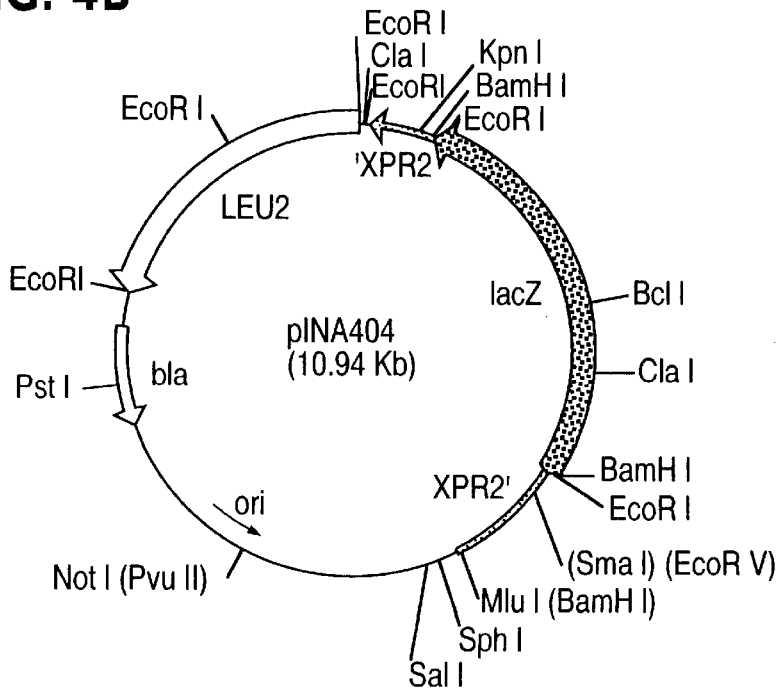
Figure 4C:
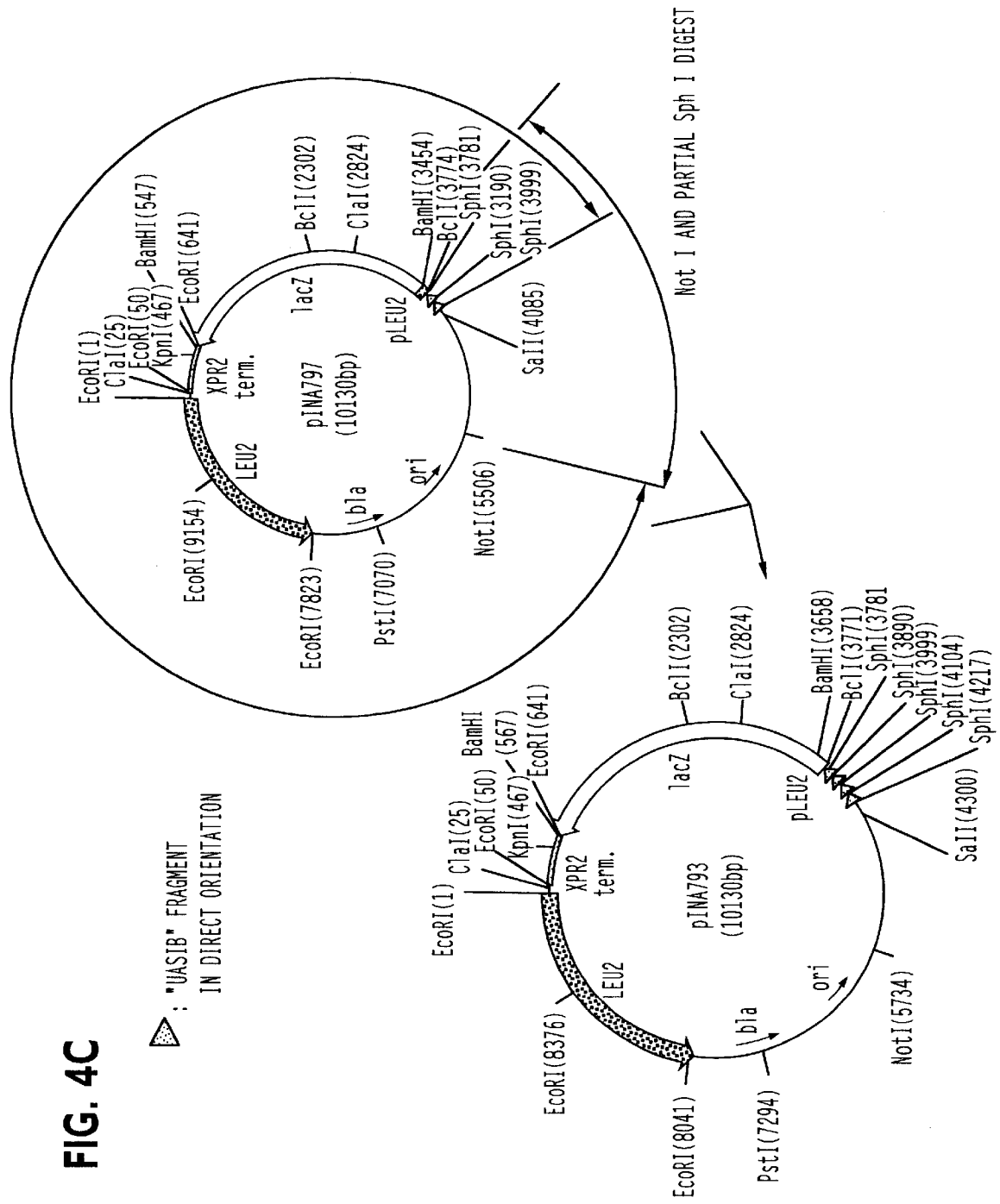

FIGS. 4A–4C: Maps of pINA354 and pINA404 plasmids and construction of plasmids with hybrid promoters carrying three or four copies of "UAS1B" (ex: pINA993).

The restriction sites or sequences that were destroyed during the construction of the plasmids are shown in parentheses. Those present at multiple locations are numerated when used during the constructions. The approximate location of oligonucleotides used in PCR reactions is indicated.
A/ map of pINA354 (Blanchin-Roland et al., 1994).
B/ map of pINA404 (Blanchin-Roland et al., 1994).

These two plasmids carry the functional XPR2 promoter directing the expression of the lacZ gene.

C/ construction of pINA993. The plasmids with hybrid promoters carrying three or four copies of "UAS1B" were derived from those carrying two copies, directly obtained in the ligation experiment of the "UAS1B" fragment into pINA781. The obtention of pINA993 from pINA797 (2 direct copies) is shown: pINA797 was digested with NotI and, partially, with SphI (conditions of partial digest giving a mean of one cut). Among the restriction fragments obtained were those shown in the figure, enabling by their ligation the formation of the pINA993 plasmid, with four tandem direct copies of "UAS1B". When only one copy of "UAS1B" was conserved in one of the fragments, pINA991 (3 direct copies) was obtained. Similarly, pINA992 (3 inverted copies) and pINA994 (4 inverted copies) were derived from pINA798 (2 inverted copies).

Figure 5A:
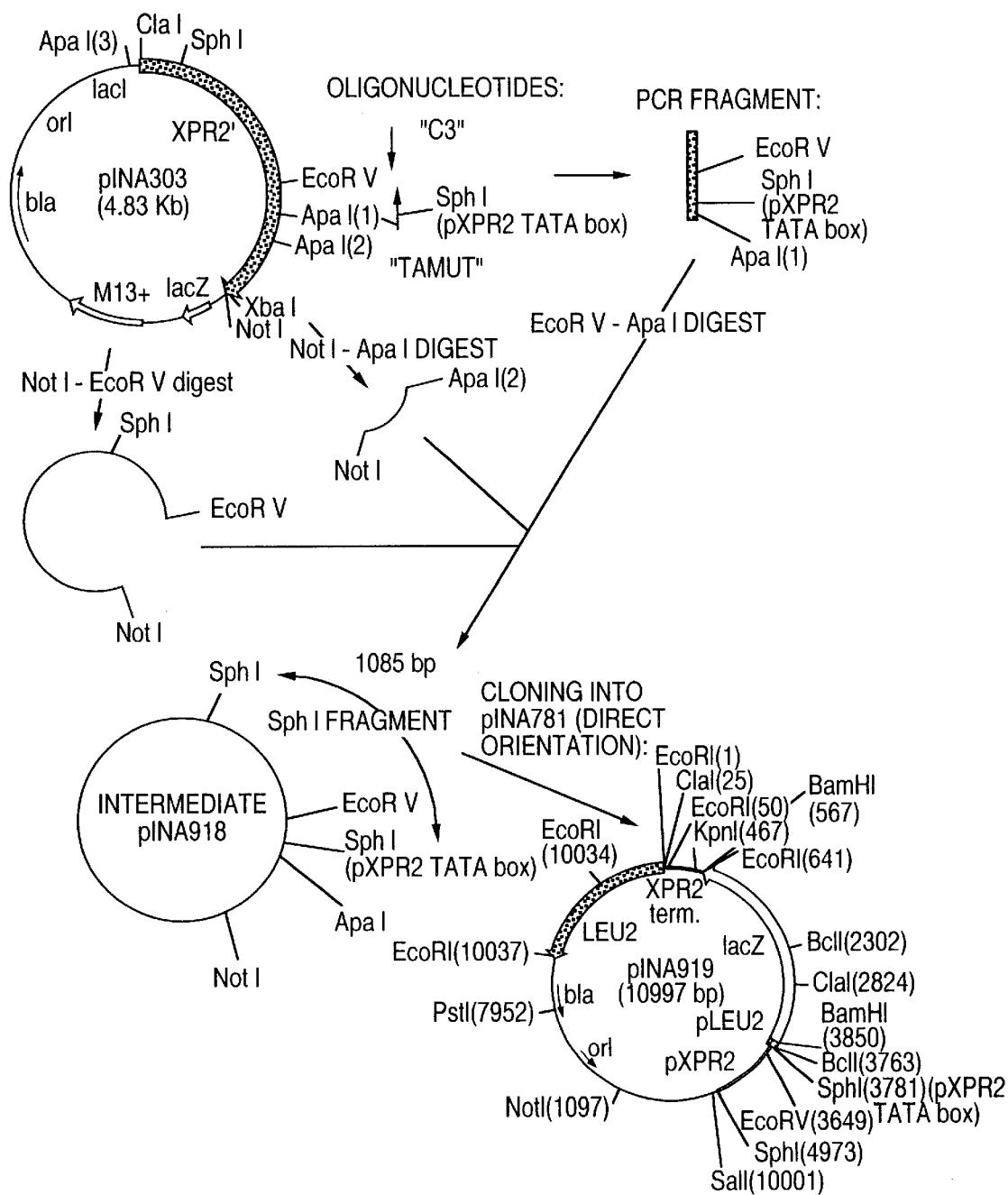
Figure 5B:
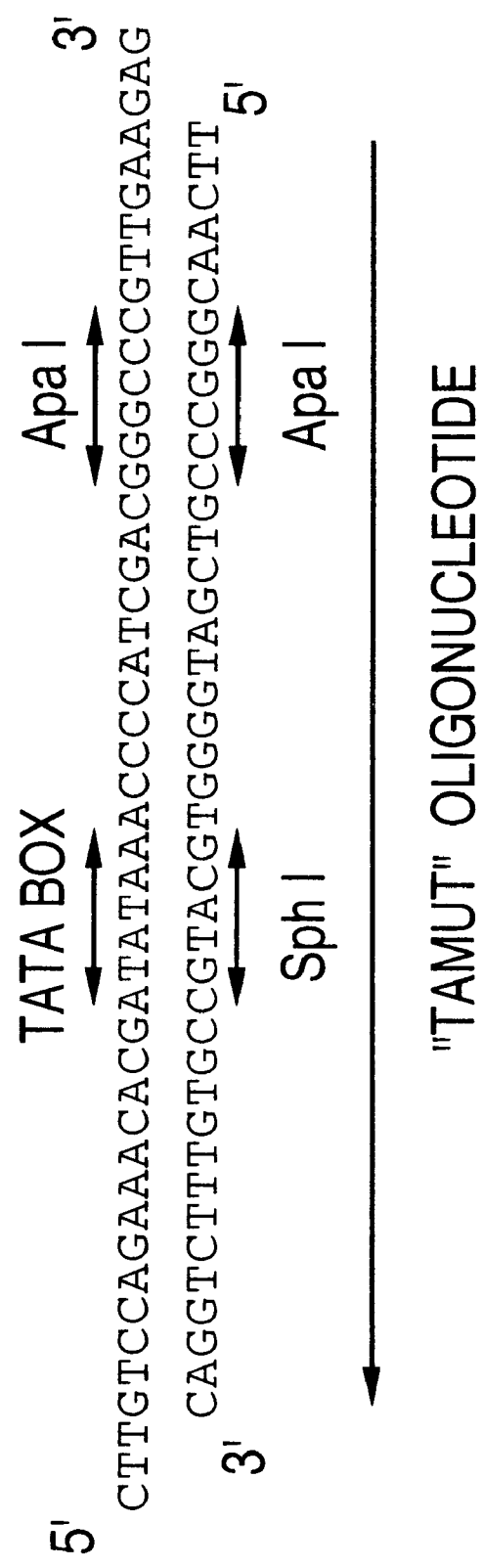

FIGS. 5A & 5B (SEQ ID NOS 18 & 19, respectively): Map of pINA303 plasmid and construction of pINA919 plasmid.

The restriction sites or sequences that were destroyed during the construction of the plasmids are shown in parentheses. Those present at multiple locations are numerated when used during the constructions. The approximate location of oligonucleotides used in PCR reactions is indicated.
A/ The pINA303 plasmid, carrying the promoter and prepro region of XPR2 gene (Blanchin-Roland et al., 1994), was used as a template to synthetize a PCR fragment, using the mutagenic oligonucleotide "TAMUT" (shown below in B/) and the following one (SEQ ID NO:9):

oligo "C3": 5' ACCATGTTTCAGCGCAATCCGACTTC-CAACCC 3'

This PCR fragment was ligated (after an EcoRV-ApaI digest) with two DNA fragments obtained from pINA303 (NotI-EcoRV and NotI-ApaI digests) to create the pINA918 plasmid as a construction intermediate. The XPR2 promoter sequence of this plasmid carries mutations that inactivate its TATA box and replace it by a new SphI site. A SphI digest gave a 1085 bp fragment, encompassing the whole TATA-deleted XPR2 promoter, that was inserted at the SphI site of pINA781, upstream of the minimal LEU2 promoter (see FIG. 3). The insertion in direct orientation, as shown in the figure, gave the pINA919 plasmid. The insertion in inverted orientation gave pINA920.
B/ sequence of the mutagenic oligonucleotide "TAMUT", carrying mutations destroying the TATA box in the XPR2 promoter and creating a new SphI restriction site.

Figure 6A:
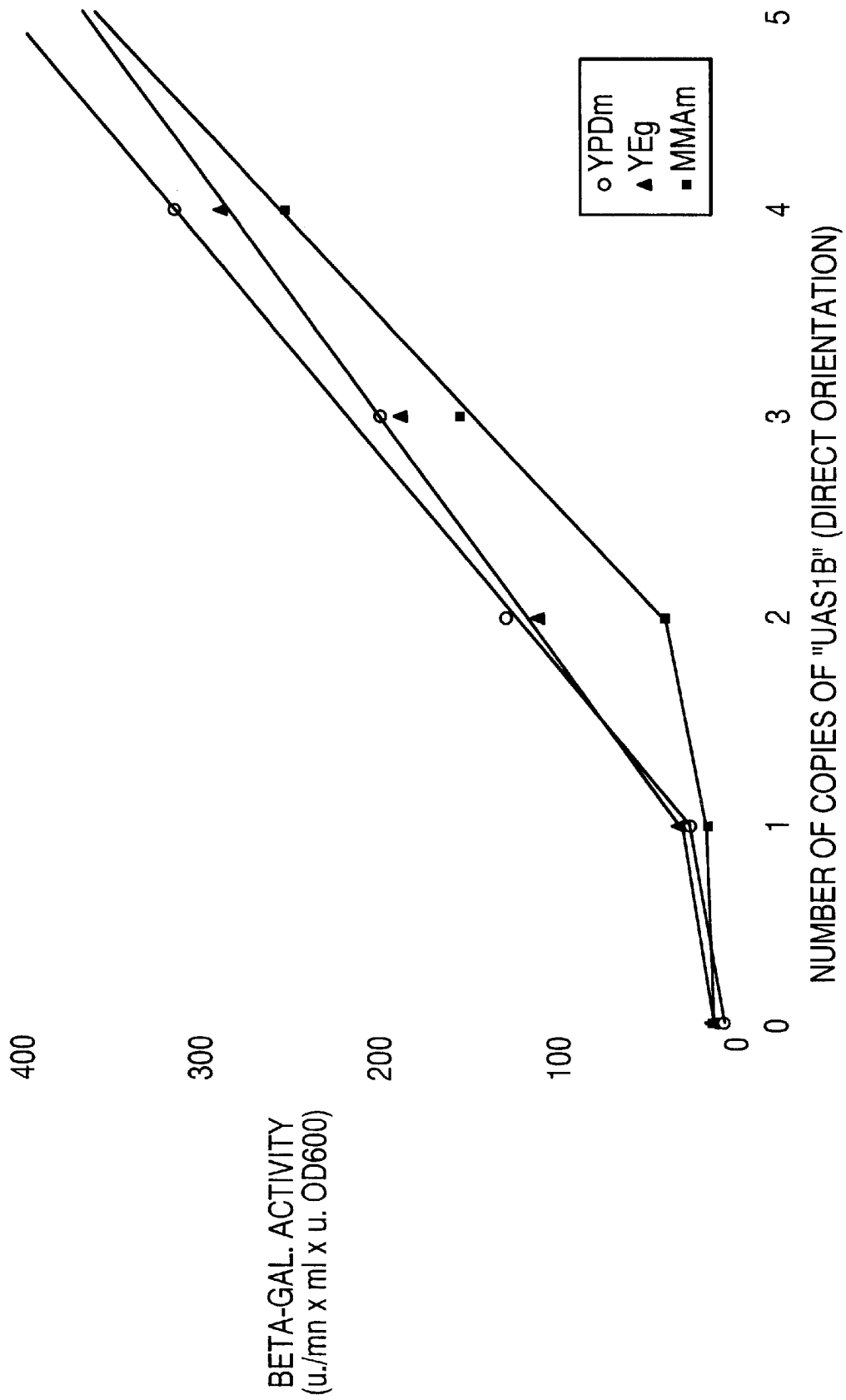
Figure 6B:
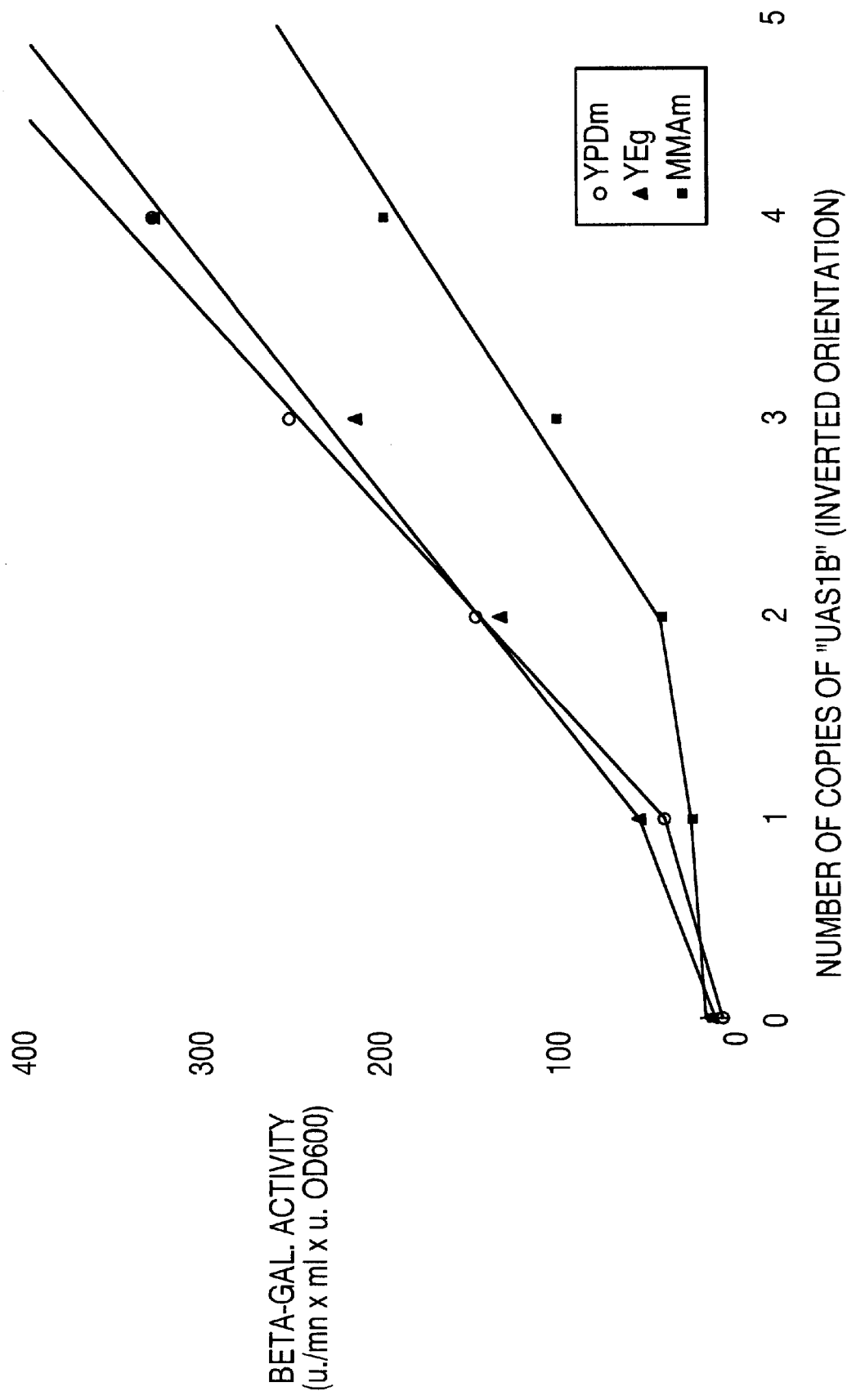

FIGS. 6A & 6B: Graphs presenting the activity of hybrid promoters as a function of the number of copies of the "UAS1B" fragment.
A/ for hybrid promoters carrying 1 to 4 tandem direct copies of "UAS1B" inserted at the SphI site of pINA781, upstream of the minimal LEU2 promoter (respectively pINA795, 797, 991 and 993).
B/ for hybrid promoters carrying 1 to 4 tandem inverted copies of "UAS1B" inserted at the SphI site of pINA781, upstream of the minimal LEU2 promoter (respectively pINA796, 798, 992 and 994).

Figure 7A:
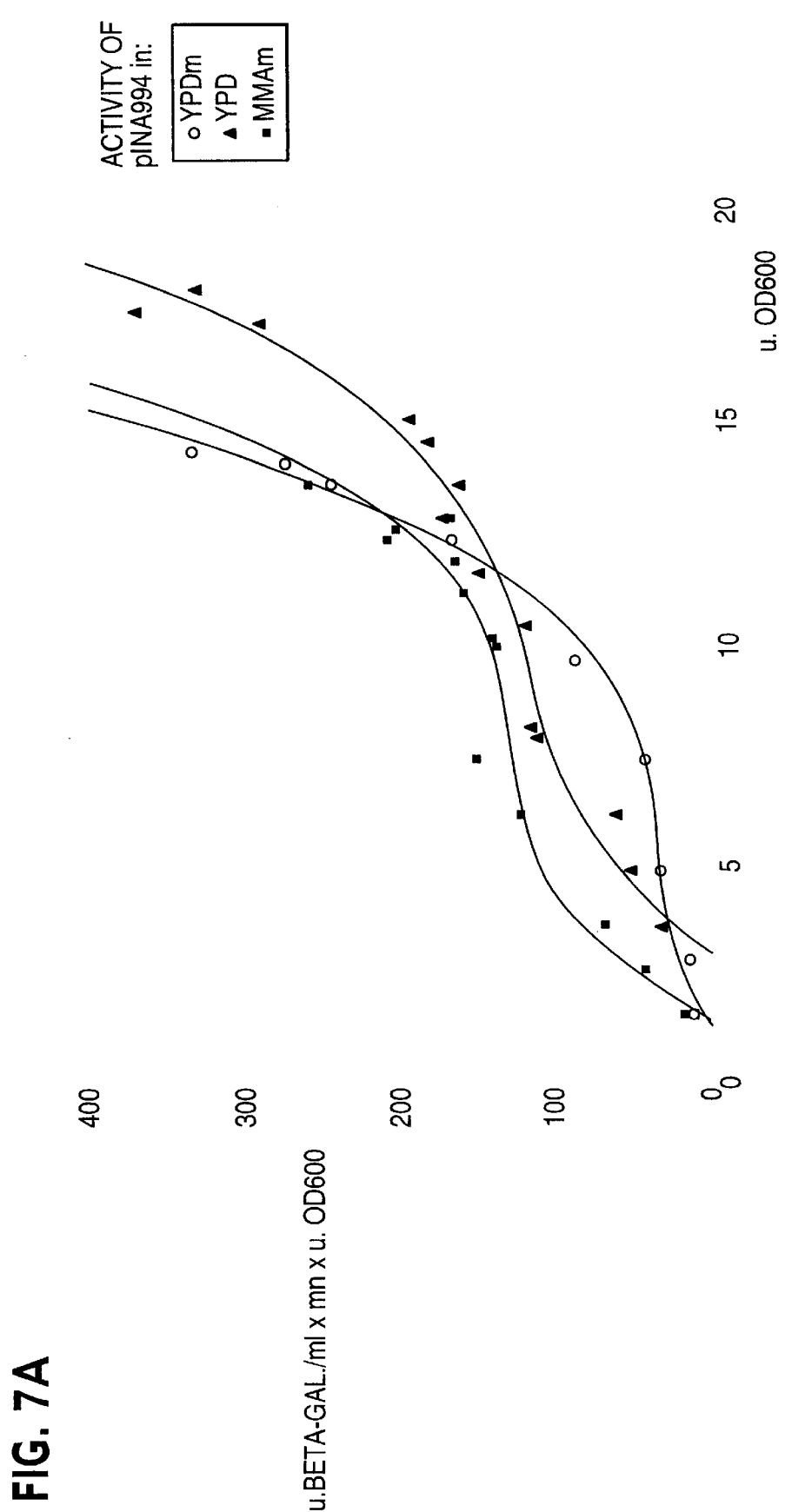
Figure 7B:
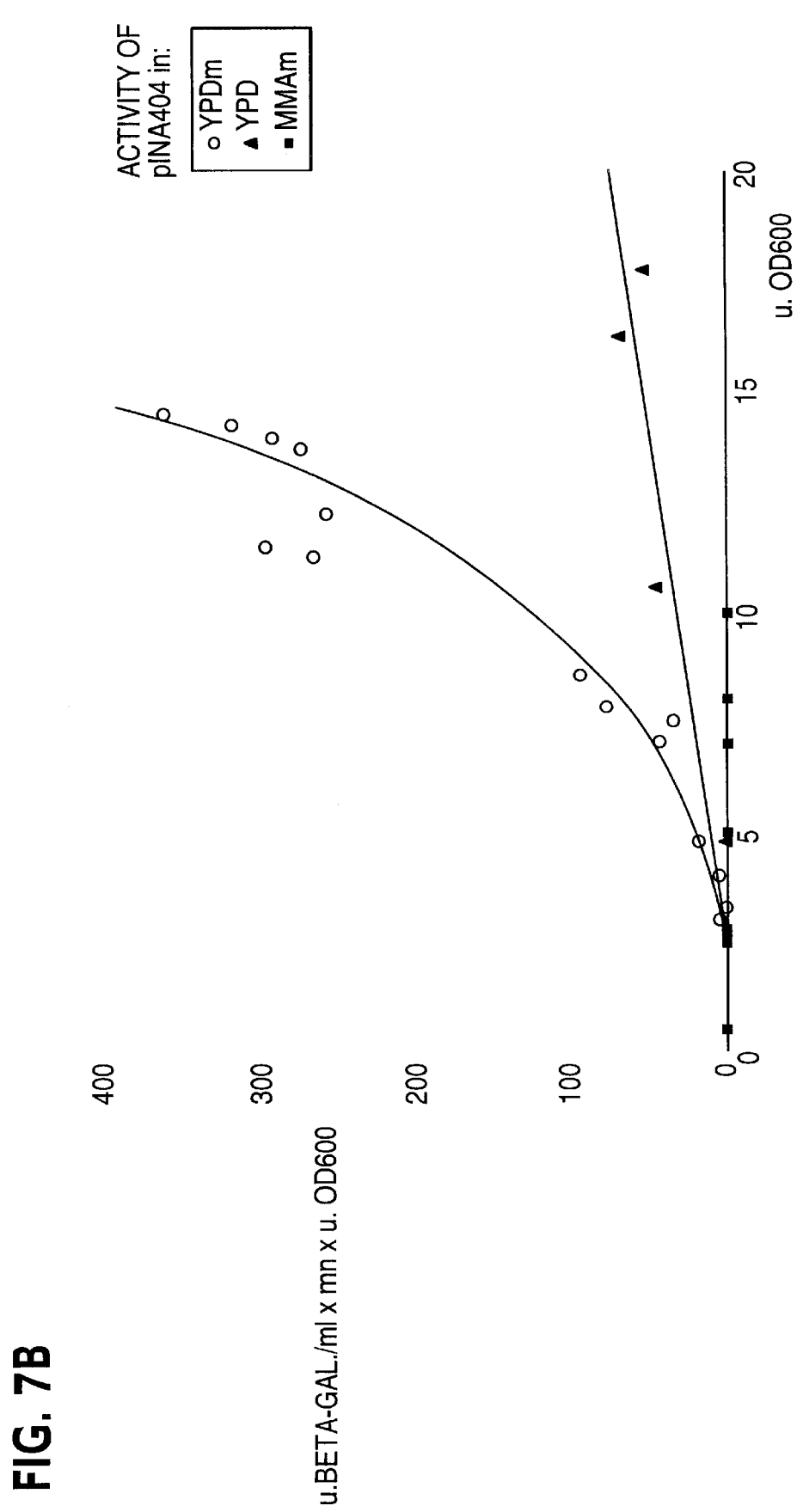
Figure 8A:
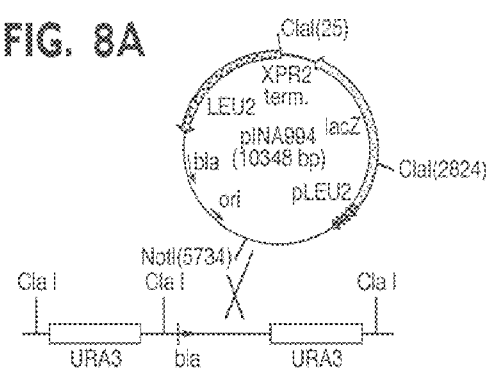
Figure 8D:
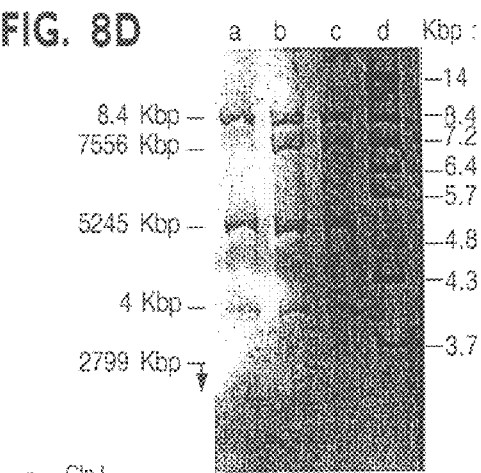
Figure 8B:
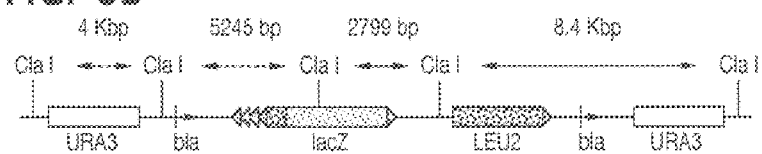
Figure 8C:
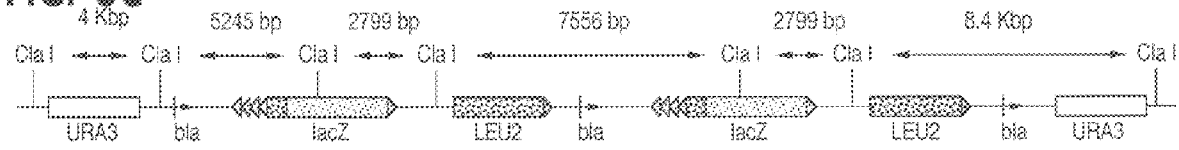

FIGS. 7A & 7B: Graphs presenting the activity of pINA994 hybrid promoter and wild type XPR2 promoter as a function of the OD600, during culture in various media.
A/ activity of the pINA994 hybrid promoter (carrying 4 inverted copies of "UAS1B"—see FIG. 4) in the inducing YPDm medium, the classical rich medium YPD or the repressing MMAm medium.
B/ activity of the wild type XPR2 promoter of pINA404 (see FIG. 4) in the same media.

FIGS. 8A–8D: Southern blotting analysis of strains carrying a single or two tandem integrated copies of pINA994.
A/ Scheme of the pBR platform of JM23SB Y. lipolytica strain and of the integration of NotI-linearized pINA994 plasmid.
B/ Restriction pattern for ClaI obtained after integration of a single copy of pINA994.
C/ Restriction pattern for ClaI obtained after integration of two tandem copies of pINA994.
D/ Southern blotting analysis of the genomic DNA of three integrants obtained with pINA994. Genomic DNA was digested with ClaI restriction enzyme. The membrane was revealed using a digoxigenin labelling kit, according to the indications of the supplier (Boehringer Mannheim), with pBR322 and lambda DNA probes.

lane a: correct integration of a single copy of pINA994.

lanes b and c: correct integration of two tandem copies of pINA994, revealed by an extra 7.5 Kb band.
(the 2.8 Kb band, visible on the original membrane in lanes a, b and c, is not shown on the photography)

lane d: migration marker (lambda DNA digested with BstEII).

Figure 9:
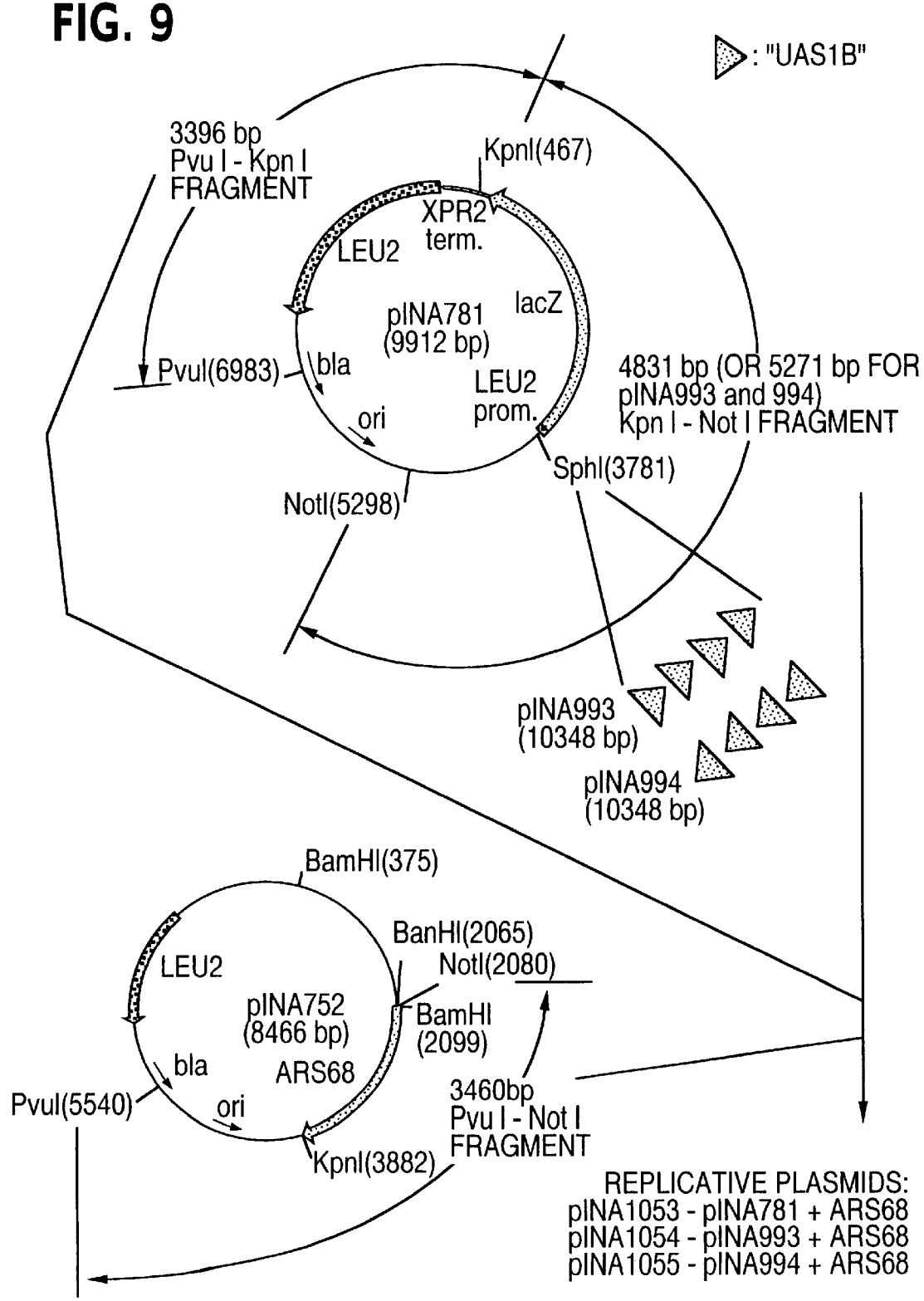

FIG. 9: Construction of the replicative plasmids carrying the optimized promoters.

The ARS-containing plasmids were obtained by ligation of three DNA fragments:
the 3460 bp PvuI-NotI fragment from pINA752 (previously described in Fournier et al., 1993): pBR322 DNA carrying ARS68.
the 3396 bp PvuI-KpnI fragment from pINA781 (The PvuI site at position 6983 is not unique: several PvuI sites are present in the LacZ gene).
the 4831 bp NotI-KpnI fragment from pINA781 for the construction of pINA1053 or, similarly, the 5271 bp NotI-KpnI fragment from pINA993 or pINA994 for the construction of, respectively, pINA1054 and pINA1055.

Figure 10A:
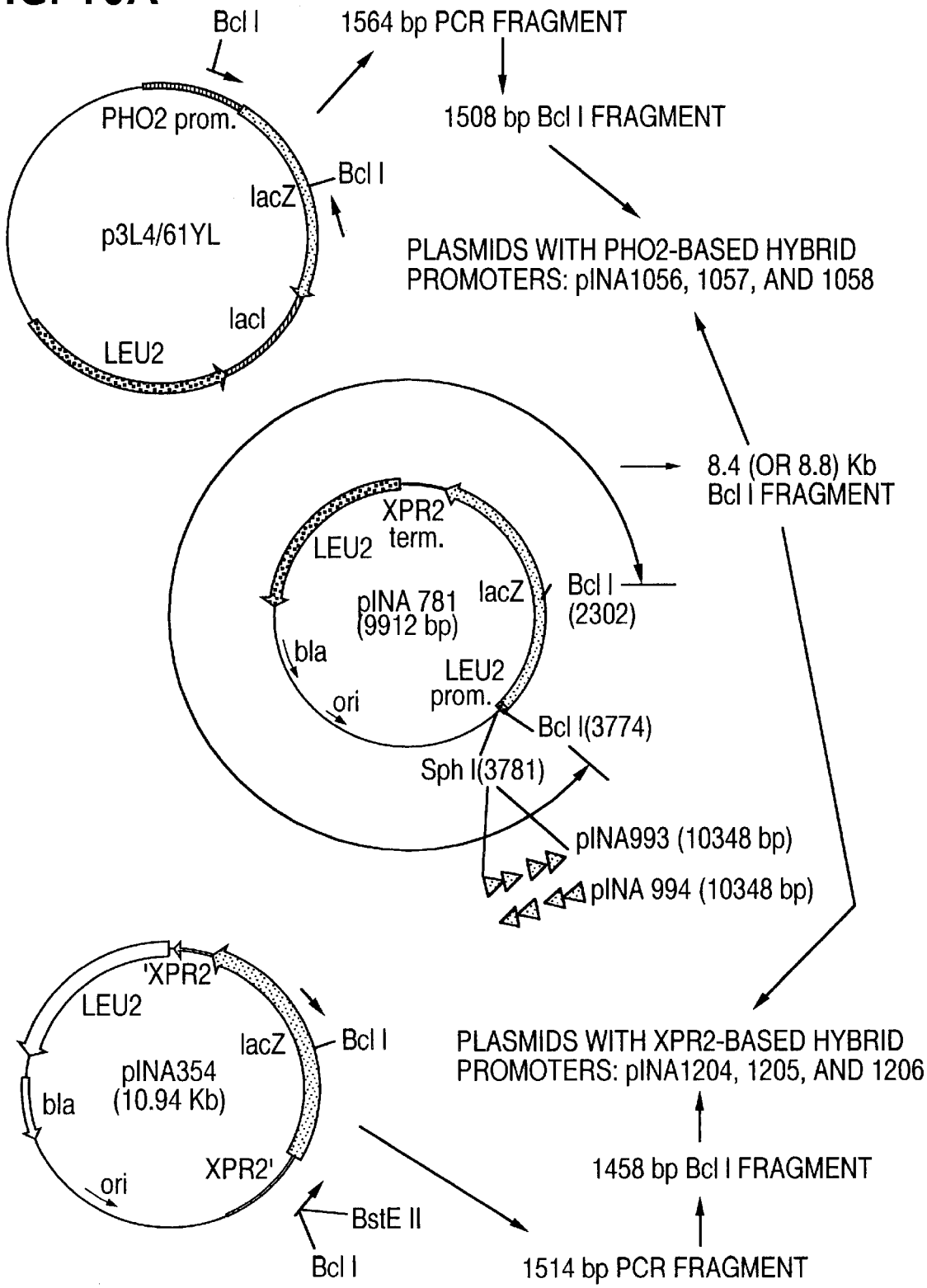
Figures 10B, 10C:
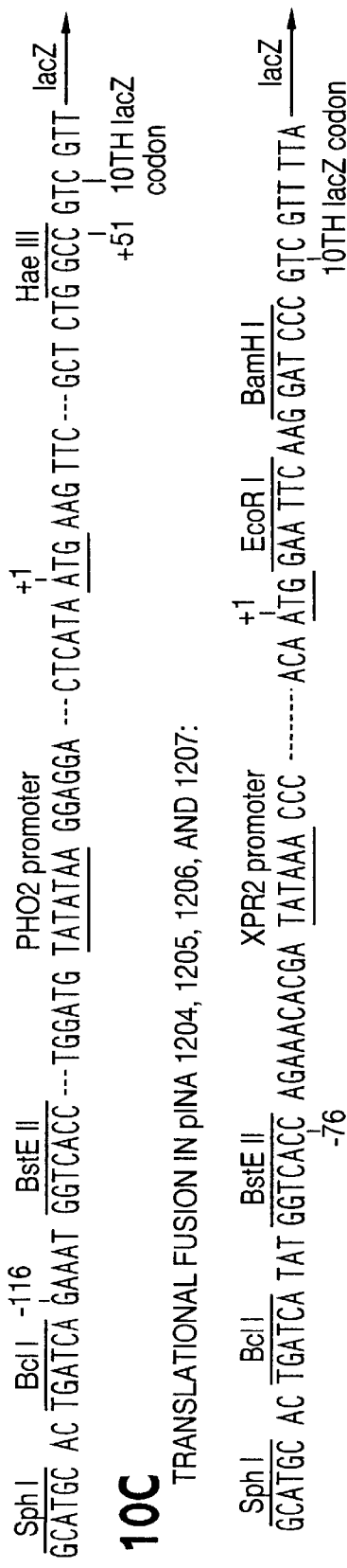

FIGS. 10A–10C (SEQ ID NOS 20 & 21, respectively): Construction of plasmids with hybrid promoters based on XPR2 or PHO2 TATA boxes.

Plasmids corresponding to pINA781, 795, 993 and 994 were constructed by replacing the TATA box and ATG region of the LEU2 gene by those of the Y. lipolytica PHO2 or XPR2 genes. The construction of pINA993 derivatives (respectively pINA1057 and pINA1205) is described in detail hereafter. The construction of pINA994 derivatives (respectively pINA1058 and pINA1206) was similar. The plasmids corresponding to pINA781 (respectively pINA1056 and pINA1204) and to pINA795 (respectively pINA1059 and pINA1207) were obtained following a total or partial SphI digestion of pINA1057 or pINA1205, followed by a self-ligation: this allowed to eliminate all "UAS1B" copies in the case of pINA1056 and 1204 or to maintain only one direct "UAS1B" copy in the case of pINA1059 and 1207.

A/ The pINA1057 and pINA1205 plasmids were constructed by replacing the 1.5 Kb BclI fragment from pINA993 by another 1.5 Kb BclI fragment, obtained after BclI digestion of a PCR fragment carrying respectively a translational fusion of the lacZ gene with either the minimal PHO2 promoter or the minimal XPR2 promoter. This 1.5 Kb region was entirely checked by sequencing in the resulting constructs.

For the PCR fragment carrying the PHO2 TATA box, the matrix used was the p3L4/61YL plasmid (previously described in Treton et al., 1992) carrying a translational fusion of the native PHO2 promoter with the lacZ gene. The upstream mutagenic oligonucleotide was (SEQ ID NO: 10):

5' GCCAAACG<u>TGATCA</u>GAAATGGTCACCCAGGAC 3'

The mutations used to create a BclI site (underlined) are in bold type. A BstEII site is present (in italic type) in the sequence of the PHO2 promoter. The downstream oligonucleotide, hybridizing to the lacZ gene sequence downstream of the BclI site, was (SEQ ID NO: 11):

5' CGTCGTGATAGCGCCG 3'

The PCR fragment obtained with these oligonucleotides contains the sequence of the PHO2 promoter from nucleotide −116 to nucleotide +51.

The sequence found for the translational fusion of the minimal PHO2 promoter with the lacZ gene was different from that expected from data described in Treton et al. (1992), revealing that the fusion in p3L4/61YL plasmid did not occur at the first HaeIII site in PHO2 ORF but in fact at the second one, 15 bp downstream. The number of codons from PHO2 ORF still present in p3L4/61YL and in our constructs is actually 17, which corresponds to the entire signal peptide. The translational fusion in pINA1057 (and pINA1056, 1058 and 1059) is shown in B/.

For the PCR fragment carrying the XPR2 TATA box, the matrix used was the pINA354 plasmid (carrying a translational fusion of the XPR2 promoter to the lacZ gene—see FIG. 4). The upstream mutagenic oligonucleotide was (SEQ ID NO: 12):

5' CAGTTTCT<u>TGATC</u>ATAT
<u>GGTCA</u>CCAGAAACACGATATAAACC 3'

The downstream oligonucleotide was the same as above. The mutations used to create respectively a BclI site and a BstEII site (underlined) are in bold type. The TATA box is indicated in italic type. The PCR fragment obtained with these oligonucleotides contains the sequence of the XPR2 promoter from nucleotide −76 to nucleotide +3. The translational fusion in pINA1205 (and pINA1204, 1206 and 1207) is shown in C/.

B/ Translational fusion in pINA1056, 1057, 1058 and 10659
C/ Translational fusion in pINA1204, 1205, 1206 and 1207

Figure 11A:
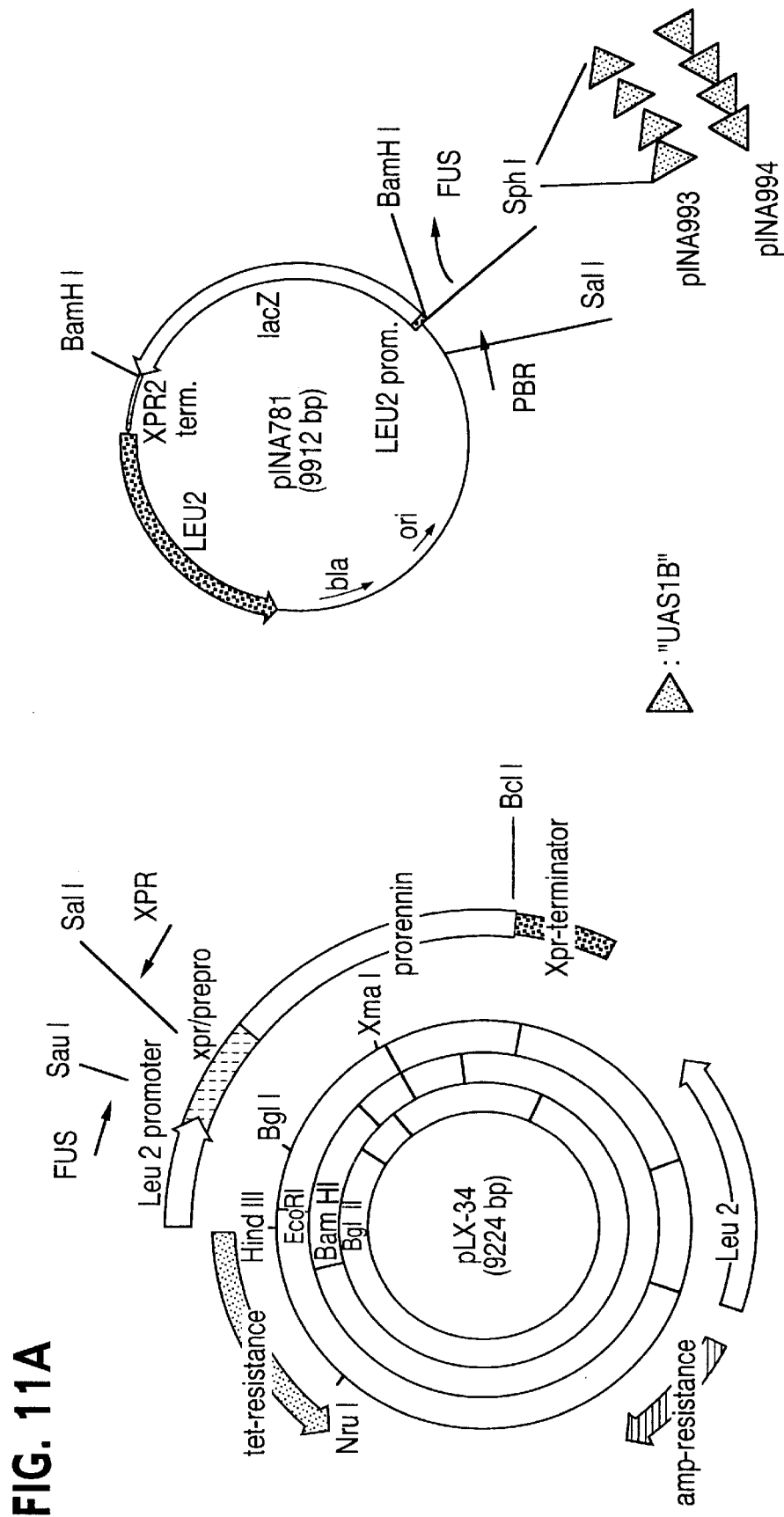
Figure 11B:
Figure 11C:
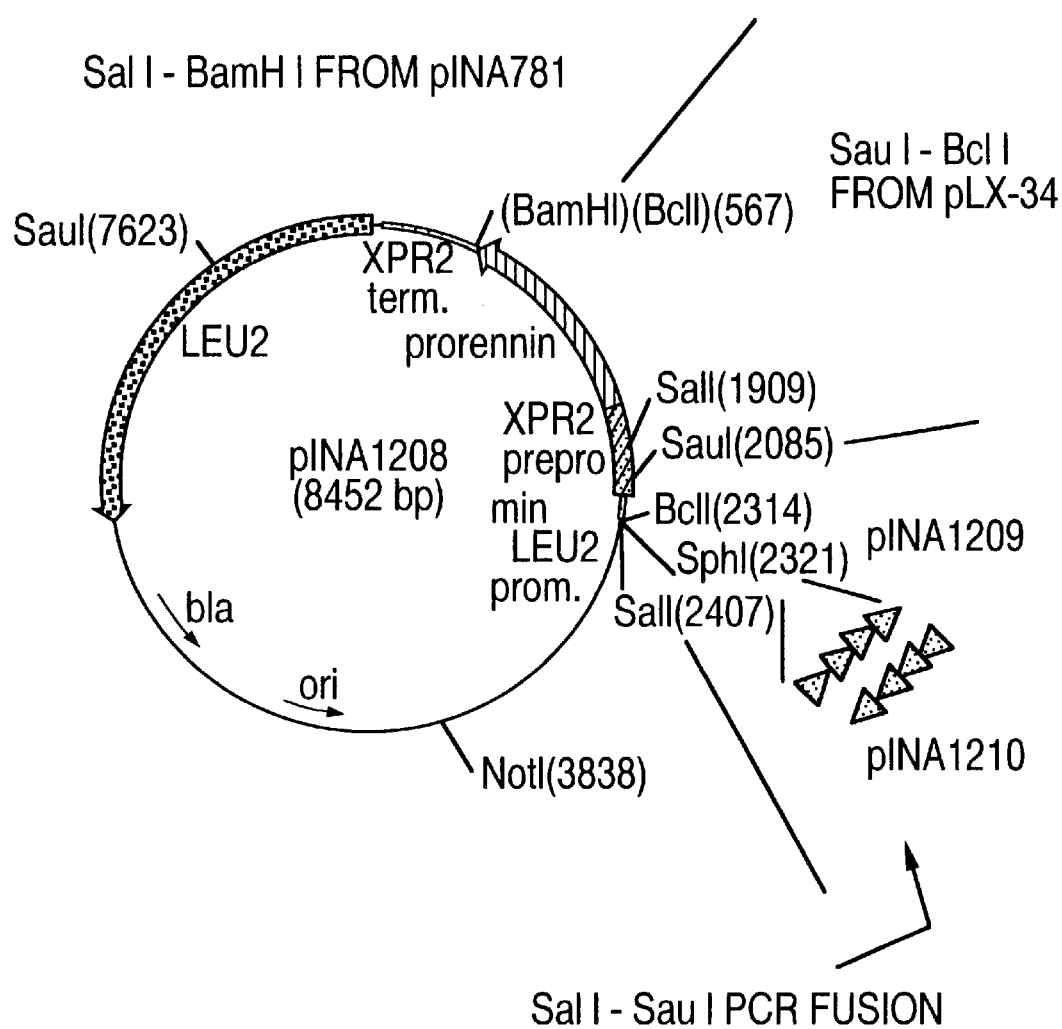

FIGS. 11A–C (SEQ ID NO: 22): Construction of plasmids for expression and secretion of prorennin A directed by hybrid promoters.

A/ Synthesis of a PCR fragment realizing the fusion [hybrid promoter: XPR2-prepro:prorennin], location of the three oligonucleotides on the two matrices B/ Scheme of the PCR fusion fragment, sequence of the three oligonucleotides C/ Construction and map of pINA1208 plasmid (and of pINA1209 and 1210).

pINA1208, 1209 and 1210, carrying respectively the hybrid promoters from pINA781, 993 and 994 were constructed using a three fragments ligation involving (as shown in C/):

the 1469 bp SauI-BclI fragment from pLX-34 plasmid, carrying the downstream part of the XPR2 prepro region, translationally fused to the entire cDNA of the prorennin A gene (the TGA sequence in the BclI site constitute the stop codon).

the 6.6 Kbp SalI-BamHI fragment from pINA781, carrying pBR322 sequence, LEU2 gene and the XPR2 terminator.

a SalI-SauI fragment obtained after digestion of a PCR fragment synthetized (as shown in A/ and B/) using two matrices (pLX-34 and pINA781, or pINA993, or pINA994) and three oligonucleotides, according to a method described in Yon and Fried (1989). This method allowed to obtain the three PCR fragments corresponding to a fusion of each of the three hybrid promoters to the XPR2 prepro region:

an upstream oligonucleotide ("PBR") hybridizes to the pBR region (upstream of each hybrid promoter) of pINA781, 993 or 994.

the fusion oligonucleotide ("FUS") hybridizes to pLX-34 in the region of the fusion between the LEU2 promoter and the XPR2 prepro region and also hybridizes partly to pINA781, 993 or 994 in the region of the minimal LEU2 promoter.

a downstream oligonucleotide ("XPR") hybridizes to the XPR2 prepro region of pLX-34 plasmid.

A PCR reaction performed with these elements allowed to realize a fusion between the hybrid promoter of pINA781 (or 993, or 994) and the prepro sequence of pLX-34. The PCR fragment obtained was digested with SalI and SauI to generate a cohesive ends fragment of 298 bp when pINA781 was used as one of the matrices, and of 734 bp when either pINA993 or 994 was used. Each of these fragments was ligated to the two fragments described above and was entirely checked by sequencing.

EXAMPLE 1

Reporter System, Culture Media and Growth Conditions

Figure 1:
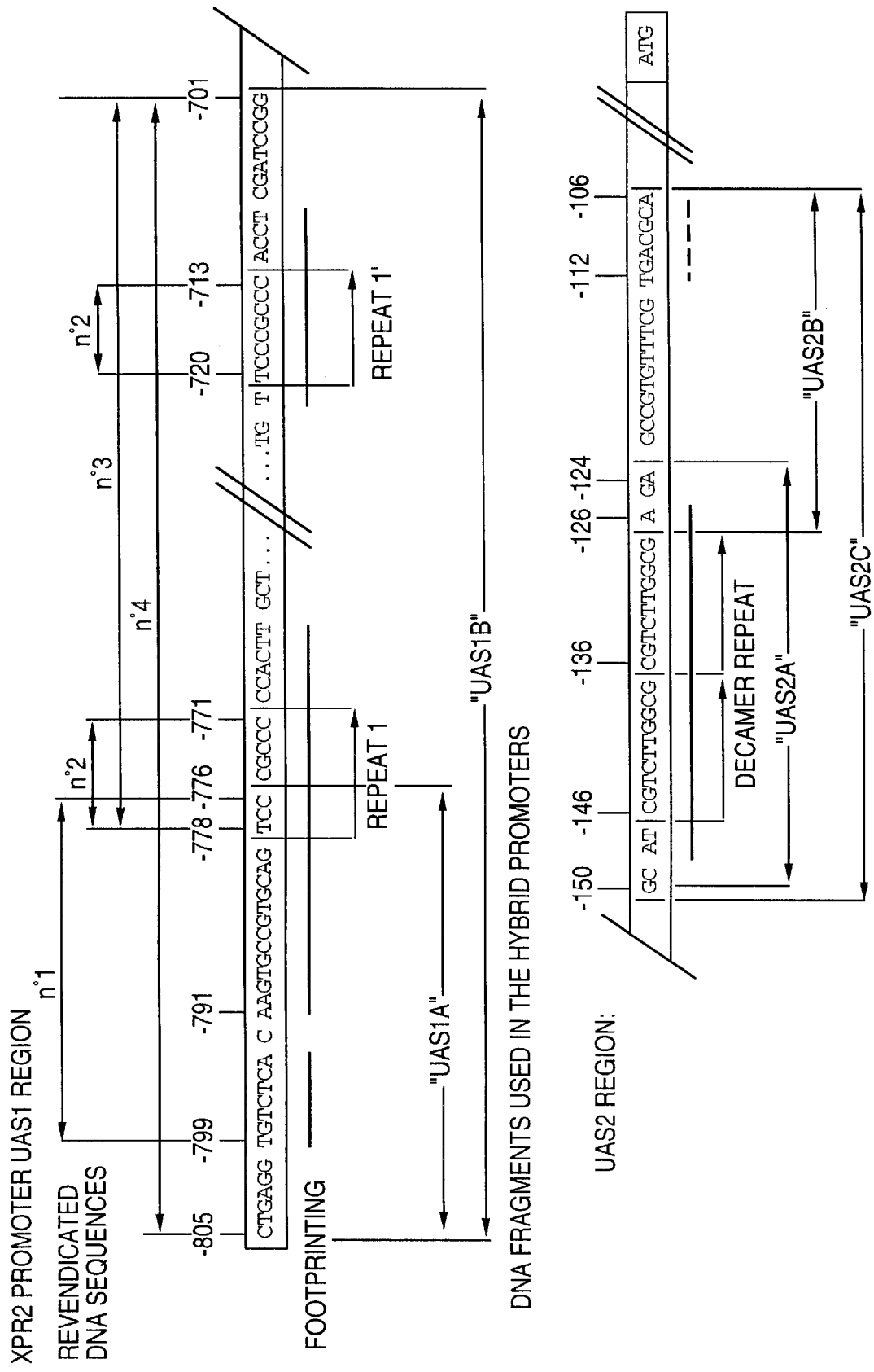
FIG. 1 (SEQ ID NOS 1–4 & 13, respectively): Schema of the UAS regions of the XPR2 promoter.

The DNA fragments from the UAS regions shown in FIGS. 1 and 2 were used to construct hybrid promoters, in order to analyse their physiological activity outside of the XPR2 context. As described in the FIGS. 2 and 4, they were inserted (in both orientations and different copy numbers) in the integrative reporter plasmid pINA781 (FIG. 3A), at the SphI restriction site, in front of the minimal LEU2 promoter (reduced to the TATA box and ATG sequence: nucleotides −94 to +18 from Y. lipolytica LEU2 gene—Gaillardin and Ribet, 1987 and FIG. 3B) directing the expression of the lacZ gene. All plasmid constructions were performed using standard molecular biology methods (Sambrook et al., 1989) and HB101 or DH5aF' E. coli strains (respectively: Sambrook et al., 1989; Raleigh et al., 1989). When cutting with dam-sensitive BclI restriction enzyme was required, the JM110 E. coli strain was used (Yanish-Perron et al., 1985).

For all integrative plasmids used in this work, the expression of the heterologous protein was measured after integration in the genome of the Yarrowia lipolytica strain JM23SB (Blanchin-Roland et al., 1994), using the method described by Davidow et al. (1985). The genotype of the JM23SB strain is the following:

MatB, leu2-35, lys5-12, ura3-18::URA3, xpr2::LYS5

The *Yarrowia lipolytica* strain JM23SB has been deposited at the "Collection Nationale de Cultures de Microorganismes" of the Institut Pasteur in Paris (France) under Accession Number I-1581.

This strain carries a pBR322 platform, provided by the integration of the pINA300' plasmid carrying the URA3 gene (Blanchin-Roland et al., 1994), that allows the subsequent integration of plasmids containing sequences from pBR322. The NotI site in pINA300', pINA354, pINA404 and their derivatives (including pINA781 and derived plasmids) is part of a polylinker inserted at the previous PvuII site of pBR322 (Blanchin-Roland et al., 1994).

The plasmids issued from pINA354 or pINA404 (pINA781 and derived plasmids) were linearized at the NotI site, in order to direct the integration at this same site in the pBR322 platform of JM23SB (Blanchin-Roland et al., 1994). The correct integration of a single copy of each plasmid in *Yarrowia lipolytica* genome was checked by Southern blot analysis, as described previously (EP 138 508).

The β-galactosidase activity of the hybrid promoters was assessed, following integration into the *Yarrowia lipolytica* genome, under different physiological conditions (inducing, basal or repressing media, see below). It was compared to that obtained with the reporter plasmid pINA781 and with pINA404, carrying the native XPR2 promoter, measured in the same conditions.

The *E. coli* strain HB101 containing plasmid pINA404 (HB101[pINA404]) has been deposited at the "Collection Nationale de Cultures de Microorganismes" of the Institut Pasteur in Paris (France) under Accession Number I-1580.

For each construction, two to four independent integrants were assayed (two to six measures performed, in duplicate, on independent cultures). β-galactosidase assays were carried out as described by Miller (1972), on stationary phase cultures. Reproducibility was in the range of ±4% between the duplicates. Data from repeated experiments was in the range of ±15%. ND=not determined.

The inducing medium (YPDm) contained 0.2% yeast extract, 0.1% glucose, and 5% proteose peptone in 50 mM sodium/potassium phosphate buffer (pH 6.8). The non-inducing (basal) medium (YEg) contained 1% yeast extract and 0.1% glucose in 50 mM sodium/potassium phosphate buffer (pH 6.8). The repressing medium (MMAm) was a modified synthetic minimal MMA medium (Gutz et al., 1974) containing 200 mM sodium/potassium phosphate buffer (pH 6.8), glycerol (1%) as a carbon source (glycerol is better catabolic repressor than glucose for AEP synthesis) and ammonium sulfate (0.2%) as a nitrogen source. When the effect of pH was tested, the YPDm medium contained 200 mM sodium citrate buffer (pH 4.0) instead of phosphate buffer. The final pH of the stationary phase cultures was checked and found to be comprised between 4.3 and 4.7. The cells grown in YPDm(pH 4.0) were pelleted and were rinsed and resuspended in 50 mM sodium/potassium phosphate buffer (pH 6.8) prior to β-galactosidase assays. The classical rich medium YPD contained 1% yeast extract, 1% bacto peptone and 1% glucose. The classical minimal medium $YNB_{N5000}$ contained 0.67% yeast nitrogen base (without amino acids) and 1% glucose.

EXAMPLE 2

Validity of the Reporter System

Materials & Methods as in Example 1

In order to test the validity of this reporter system, we first checked that the complete upstream sequence of the XPR2 promoter devoid of its own TATA box was able to impose a XPR2-like regulation to the minimal LEU2 promoter (the effect of the pH is analysed hereafter: see Example 4, Table 4).

As described in the FIG. 5, the TATA box of the native XPR2 promoter (determined from Davidow et al., 1987) was mutated to a new SphI restriction site, using PCR directed mutagenesis. This enabled the insertion of a SphI restriction fragment encompassing the physiologically active promoter (devoid of its TATA box) into pINA781, upstream of the minimal LEU2 promoter, in the direct (pINA919) or inverted orientation (pINA920).

The Table 1 shows the β-galactosidase activities of *Y. lipolytica* JM23SB strains carrying integrated plasmids with TATA-deleted XPR2 promoters, in different media.

The regulation pattern observed with the constructs containing the TATA-deleted XPR2 promoter inserted into pINA781 was similar to that of the native promoter. The level of repression obtained in MMAm was however slightly less important, perhaps reflecting the influence of the LEU2 TATA box.

This experiment justifies that our reporter system is able to reproduce the regulation pattern of the native XPR2 promoter.

TABLE 1

β-galactosidase activities of *Y. lipolytica* JM23SB strains carrying integrated plasmids with TATA-deleted XPR2 promoter, in different media.

| | | β-galactosidase activity (u β-gal/ml × mn × u $OD_{600}$) | | |
| --- | --- | --- | --- | --- |
| promotor | plasmid | inducing YPDm medium | basal YEg medium | repressing MMAm medium |
| minimal LEU2 promoter | pINA781 | 10.8 | 20.2 | 20.0 |
| TATA-deleted XPR2 promoter + minimal LEU2 promoter | | | | |
| direct | pINA919 | 325.7 | 40.1 | 7.4 |
| inverted | pINA920 | 145.8 | 31.0 | 13.7 |
| native XPR2 promoter | pINA404 | 303.2 | 70.2 | 1.6 |

EXAMPLE 3

Analysis of the Distal UAS1 Region of the XPR2 Promoter

Materials & Methods as in Example 1

The DNA fragments from the UAS1 region used in this analysis are shown in the FIGS. 1 and 2. "UAS1A" was obtained by hybridization of two synthetic oligonucleotides (see FIG. 2); it consists essentially of the sequence bounded by the nucleotides −805 and −776 of the sequence of the XPR2 promoter. "UAS1B" was obtained by PCR (see FIG. 2); it consists essentially of the sequence bounded by the nucleotides −805 and −701 of the sequence of the XPR2 promoter. The SphI restriction sites or cohesive ends of the fragments allowed their insertion at the SphI site of pINA781, upstream of the minimal LEU2 promoter (see FIG. 3).

Plasmids carrying "UAS1A" or "UAS1B" fragments, in one copy or two tandem copies and in both orientations were obtained and are described in the Table 2. This Table shows the β-galactosidase activity of *Yarrowia lipolytica* JM23SB strains carrying these integrated plasmids, in different media.

The "UAS1A" fragment was able to mediate a slight UAS effect, more visible with two copies. The larger "UAS1B" fragment exhibited a higher activity. In both cases, the enhancement obtained with two copies was more than additive, showing a cooperation between the elements.

No clear repression was observed for either fragment in MMAm medium; the activity was even enhanced with two copies of "UAS1B".

The "UAS1B" fragment is unable to mediate the repression by the carbon and nitrogen sources and is therefore a good candidate for the construction of a constitutive promoter (see Example 4).

TABLE 2

β-galactosidase activity of *Yarrowia lipolytica* JM23SB strains carrying integrated plasmids with hybrid promoters containing DNA fragments from UAS1 region, in different media.

| insert upstream of minimal LEU2 promoter: | plasmid | β-galactosidase activity (u β-gal/ml × mn × u $OD_{600}$) | | |
|---|---|---|---|---|
| | | inducing YPDm medium | basal YEg medium | repressing MMAm medium |
| none | pINA781 | 10.8 | 20.2 | 20.0 |
| 1 direct "UAS1A" copy | pINA791 | 16.8 | 18.7 | 9.8 |
| 1 inverted "UAS1A" copy | pINA792 | 22.2 | ND | ND |
| 2 direct "UAS1A" copies | pINA793 | 52.1 | ND | ND |
| 2 inverted "UAS1A" copies | pINA794 | 61.6 | 44.8 | 9.6 |
| 1 direct "UAS1B" copy | pINA795 | 32.3 | 37.0 | 20.5 |
| 1 inverted "UAS1B" copy | pINA796 | 43.6 | 57.0 | 27.9 |
| 2 direct "UAS1B" copies | pINA797 | 132.6 | 115.5 | 45.2 |
| 2 inverted "UAS1B" copies | pINA798 | 150.4 | 137.2 | 46.3 |
| XPR2 native promoter: | pINA404 | 303.2 | 70.2 | 1.6 |

EXAMPLE 4

Design of Optimized Promoters

Materials & Methods as in Example 1

In order to obtain a strong constitutive promoter, we constructed hybrid promoters carrying three or four tandem copies of the "UAS1B" fragment, all direct or all inverted. Their construction is described in the FIG. 4C.

The Table 3 shows the β-galactosidase activities of *Y. lipolytica* JM23SB strains carrying integrated plasmids with different copy numbers of the "UAS1B" fragment, in different media.

The activity in the three media increased with the number of copies of "UAS1B". The constructs with four copies, pINA993 and pINA994, exhibited a very high activity in the three media, of the same order of magnitude than that of the native XPR2 promoter under inducing conditions.

The hybrid promoters of pINA993 and pINA994 are no longer repressed by the carbon and nitrogen sources and do not require the addition of peptones in the culture medium. They are able to support a strong quasi-constitutive expression and are useful for the efficient production of heterologous proteins in *Y. lipolytica*.

As shown in the graphs (FIG. 6), in YPDm and YEg media, the enhancement of activity was more than additive for two copies, and became then only additive for each new added copy (the points become aligned). In the MMAm medium, the addition of a third copy still enabled a more than additive increase.

The Table 4 shows the effect of the pH of the culture medium on the β-galactosidase activity of *Y. lipolytica* JM23SB strains carrying the optimized promoters.

A dramatic repressing effect was observed on the expression of the wild type XPR2 promoter (pINA404) when the pH of the YPDm medium was lowered to 4.0. The repressing effect was slightly lower, but still very strong with the construct carrying the entire XPR2 promoter, deleted from its TATA box, inserted in the reporter plasmid pINA781 (pINA919).

Thus, our reporter system allows the detection of the repressing effect of the pH of the culture medium: the XPR2 promoter devoid of its own TATA box was able to impose an XPR2-like pH regulation to the minimal LEU2 promoter.

The expression (in YPDm medium) of the hybrid promoters carrying four copies of "UAS1B" (pINA993 and 994) was independent from the pH of the culture: it remained at a similar high level when the pH was 4.0, although these acidic conditions strongly repressed the wild type XPR2 promoter.

TABLE 3

β-galactosidase activities of *Y. lipolytica* strains JM23SB carrying integrated plasmids with different copy numbers of the "UAS1B" fragment, in different media.

| | β-galactosidase activity (u β-gal/ml × mn × u $OD_{600}$) | | | | | |
|---|---|---|---|---|---|---|
| | YPDm inducing medium | | YEg basal medium | | MMAm repressing medium | |
| pINA781 | 10.8 | | 20.2 | | 20.0 | |
| pINA781 with | orientation: | | | | | |
| "UAS1B" inserts: | direct | inverted | direct | inverted | direct | inverted |
| 1 copy | pINA795 32.3 | pINA796 43.6 | pINA795 37.0 | pINA796 57.0 | pINA795 20.5 | pINA796 27.9 |
| 2 copies | pINA797 132.6 | pINA798 150.4 | pINA797 115.5 | pINA798 137.2 | pINA797 45.2 | pINA798 46.3 |
| 3 copies | pINA991 204.0 | pINA992 256.0 | pINA991 191.5 | pINA992 218.1 | pINA991 157.5 | pINA992 103.9 |
| 4 copies | pINA993 319.3 | pINA994 332.4 | pINA993 294.0 | pINA994 332.8 | pINA993 256.4 | pINA994 186.6 |
| pINA404 | 303.2 | | 70.2 | | 1.6 | |

TABLE 4 effect of the pH in the culture medium on the β-galactosidase activity of
Y. lipolytica JM23SB strains carrying hybrid promoters.

| insert upstream of minimal LEU2 promoter: | plasmid | β-gal. activity (u β-gal/ml × mn × u $OD_{600}$) in YPDm medium at different pHs: | |
|---|---|---|---|
| | | pH 4.0 | pH 6.8 |
| none | pINA781 | 10.0 | 10.8 |
| 1 direct "UAS1B" copy | pINA795 | 26.3 | 32.3 |
| 2 direct "UAS1B" copies | pINA797 | 75.4 | 132.6 |
| 4 direct "UAS1B" copies | pINA993 | 338.6 | 319.3 |
| 4 inverted "UAS1B" copies | pINA994 | 325.6 | 332.4 |
| TATA-deleted XPR2 promoter (direct) | pINA919 | 26.1 | 325.7 |
| XPR2 native promoter: | pINA404 | 3.6 | 303.2 |

The hybrid promoter carrying several copies of the "UAS1B" fragment exhibits a strong quasi-constitutive expression, independent of the pH of the culture medium.

The evolution of the β-galactosidase expression of pINA994 (four inverted copies of "UAS1B") during the culture growth was analysed in the inducing YPDm medium (pH 6.8), the repressing MMAm medium and the classical rich culture medium YPD (FIG. 7A). The maximum $OD_{600}$ attained by the culture was around 14–15 units in YPDm, around 10–12 units in MMAm and around 18–19 units in YPD.

For the native XPR2 promoter (pINA404), only the culture in YPDm reached high activities (FIG. 7B). The activities attained in YPD were similar to those in the basal YEg medium (see construct pINA404 in previous tables and below). The activities in MMAm remained very low.

For pINA994, the activities in the three media were of the same order of magnitude. They increased earlier in the culture (especially in MMAm) and more regularly. The maximum activity attained in YPD was slightly higher than in YPDm.

The Table 5 shows the β-galactosidase activities of Y. lipolytica JM23SB strains carrying integrated plasmids with four copies of "UAS1B" fragment, in YPD medium (stationary phase cultures). In this medium, the activities of pINA993 and pINA994 were higher (around 420 u) than in the inducing medium (around 330 u).

Therefore, the hybrid promoter of pINA994 can be used either in the classical rich culture medium YPD, or in a defined minimal medium, to drive expression at levels similar to those reached with the native XPR2 promoter in the complex YPDm medium (namely, under inducing conditions).

TABLE 5

β-galactosidase activity of Y. lipolytica JM23SB strains
carrying integrated plasmids with optimized promoters in the
classical YPD rich medium.

| insert upstream of minimal LEU2 promoter: | plasmid | β-galactosidase activity (u β-gal/ml × mn × $OD_{600}$) |
|---|---|---|
| none | pINA781 | 12.1 |
| 4 direct "UAS1B" copies | pINA993 | 418.4 |
| 4 inverted "UAS1B" copies | pINA994 | 429.0 |
| XPR2 native promoter | pINA404 | 65.1 |

TABLE 6

β-galactosidase activity of Y. lipolytica JM23SB strains
carrying one single or two tandem integrated copies of pINA994
plasmid (4 inverted "UAS1B" copies), in different media.

| | β-galactosidase activity (u β-gal/ml × mn × $OD_{600}$) | | | |
|---|---|---|---|---|
| integration at the pBR platform of: | inducing YPDm med. | basal YEg med. | repressing MMAm med. | rich YPD med. |
| one single copy of pINA994 | 332.4 | 332.8 | 186.6 | 429.0 |
| two tandem copies of pINA994 | 631.5 | 616.4 | 326.8 | 853.4 |

Two independent integrants carrying two tandem copies of pINA994 were analysed. For culture, the β-galactosidase activity was measured in duplicate.

EXAMPLE 5

Double Tandem Integration of a Plasmid with Hybrid Promoter

Materials & Methods as in Example 1

Following the integrative transformation of JM23SB Y. lipolytica strain with the pINA994 plasmid (hybrid promoter with 4 inverted copies of "UAS1B"), two integrants were found to carry a tandem integration of two copies of the plasmid. Their analysis by Southern blotting is shown in the FIG. 8. The b-galactosidase activity of these integrants was measured (Table 6) and found to be roughly twice that of an integrant with a single copy of pINA994, in inducing, basal, repressing media and in YPD medium. These results clearly indicate that the integration of several copies of a plasmid carrying the optimized promoter allows to increase the expression of the heterologous protein.

EXAMPLE 6

Replicative Yarrowia lipolytica Plasmids Carrying the Optimized Promoters

Unless specified, Materials & Methods as in Example 1

In order to test the hybrid promoters described in the Example 4 on autonomously replicating plasmids, the Y. lipolytica ARS68 was inserted into pINA993 and pINA994 (carrying respectively 4 direct and 4 inverted copies of "UAS1B") and in the reporter plasmid pINA781 (LEU2 TATA box). The ARS68 sequence was described previously in the French Patent 88-00973 and in Fournier et al. (1991). The following replicative plasmids were constructed (using E. coli DK1 strain; Raleigh et al., 1989), as described in the FIG. 9:

pINA1053 derived from pINA781 by insertion of ARS68
pINA1054 derived from pINA993 by insertion of ARS68
pINA1055 derived from pINA994 by insertion of ARS68

Plasmidic DNA from pINA1053, 1054 and 1055 was electroporated into Y. lipolytica JM23SB strain, as described previously in Fournier et al. (1993). The transformation efficiencies are shown in the Table 7 and were similar to that obtained for the replicative pINA752 plasmid (ARS68 and LEU2 gene into pBR322, Fournier et al., 1993). No transformants were obtained when electroporating control integrative plasmids (either linearized or not), as expected (since, for unknown reasons, plasmids cannot be integrated in Y. lipolytica following electroporation—Fournier et al., 1993). This suggests that all constructs replicated efficiently in Y. lipolytica. Several independent transformants were selected on minimal medium plates and analyzed further.

Two transformants of each construction were tested (with slight modification from Fournier et al., 1991) for the loss of the plasmid in non-selective complete medium (YPD): complete medium was inoculated with 5.105 cells/ml and incubated for 6 h ½ at 28° C. The cells were plated on complete medium and then replicated on minimal (YNBN5000) and complete medium plates. These two replica plates were compared to determine the percentage of plasmid-carrying Leu$^+$ cells, under non-selective conditions. The results are shown in the Table 8. After 3 to 4 generations in non-selective medium, the proportion of Leu$^+$ cells in the culture was similar for the two transformants carrying pINA1053, or 1054, or 1055, and for pINA752, namely in the range of 60–70%. This shows that these expression plasmids do not confer any detectable selective disadvantage to the transformants.

TABLE 7

Transformation efficiencies of ARS-carrying plasmids, electroporated into Y. lipolytica JM23SB strain.

| plasmid | construction | transformation efficiency |
| --- | --- | --- |
| pINA1053 | ARS68 in pINA781 | $1.5.10^5$ transformants/mg |
| pINA1054 | ARS68 in pINA993 | $2.10^5$ transformants/mg |
| pINA1055 | ARS68 in pINA994 | $7.5.10^4$ transformants/mg |
| pINA752 | ARS68 + LEU2 in pBR322 | $8.5.10^4$ transformants/mg |

TABLE 8

Plasmid loss during culture in non-setsective YPD medium.

| plasmid/transformant | nb of generations | Leu$^+$ cells |
| --- | --- | --- |
| pINA1053/1 | >3 | 68% |
| pINA1053/2 | >4 | 66% |
| pINA1054/1 | >3 | 61% |
| pINA1054/2 | >3 | 66% |
| pINA1055/1 | >4 | 69% |
| pINA1055/2 | >4 | 71% |
| pINA752 | >4 | 68% |

These tests also confirm that the pINA1053, 1054 and 1055 plasmids contain a fully functional ARS68 and constitute replicative plasmids behaving similarly to pINA752.

The plasmidic and genomic DNA from JM23SB strain transformed with pINA1053, 1054 or 1055 plasmids was extracted, as previously described (Hoffman and Winston, 1987) and used to transform E. coli DK1 strain (Raleigh et al., 1989). This "rescue" experiment allowed to obtain numerous ampicillin-resistant transformants and several of these were analysed further. The absence of rearrangements in the rescued plasmids was checked using BamHI (giving three DNA fragments ranging from 1659 to 6937 bp) and EcoRV (giving six DNA fragments ranging from 273 to 4829 bp) restriction digests. The rescued pINA1053, 1054 and 1055 plasmids were found to exhibit the same restriction patterns than the native ones (data not shown). The region of the hybrid promoters was analysed more precisely by a PCR reaction involving two flanking oligonucleotides ("LB", described in the commentary to FIG. 3, and "PBR", described in the commentary to FIG. 11). In each case, a unique band of the expected size was obtained (data not shown), showing that this region was not rearranged during passage in yeast (in particular, the four copies of "UAS1B" were conserved in the rescued pINA1054 and 1055).

The b-galactosidase activity of strains carrying the ARS-containing plasmids was measured, for different transformants, on stationary phase cultures in minimal medium (MMAm). In parallel, an aliquot of the same cultures was taken during the pre-stationary phase and used to determine the percentage of cells carrying plasmids in the culture, under selective conditions, as described above. These values are shown in the Table 9, with the results of the b-galactosidase tests.

The values vary slightly between the transformants, for each plasmid, but the differences are in the range usually observed between independent cultures. The mean value for pINA1053 (53 u) is 2.5 fold higher than previously observed for pINA781 (20 u), the mean percentage of prototrophs being 78%. In contrast, the mean values for pINA1054 (216 u) and pINA1055 (185 u) are of the same order of magnitude than those previously observed for pINA993 and 994, respectively 256 and 187 u, the mean percentage of prototrophs being 82–83% in both cases. The replicative plasmids carrying the optimized promoters do not seem to drive a higher expression level than the corresponding integrative plasmids.

TABLE 9

β-galactosidase activity of Y. lipolytica JM23SB strains carrying replicative plasmids in selective MMAm medium.

| promoter | plasmid/ transformant | Leu$^+$ cells | β-gal. activity (u β-gal/ml × mn × OD$_{600}$) |
| --- | --- | --- | --- |
| minimal LEU2 promoter | pINA1053/1 | 77.5% | 54.0 |
|  | pINA1053/2 | 78.1% | 52.9 |
|  |  |  | mean value = 53.4 u |
| same plus four direct "UAS1B" copies | pINA1054/1 | 82.4% | 198.1 |
|  | pINA1054/2 | 88.4% | 192.2 |
|  | pINA1054/3 | 78.8% | 205.0 |
|  | pINA1054/5 | 82.4% | 267.6 |
|  | pINA1054/6 | ND | 272.9 |
|  |  |  | mean value = 227.2 u |
| same plus four inverted "UAS1B" copies | pINA1055/1 | 80.5% | 162.5 |
|  | pINA1055/4 | 82.3% | 201.5 |
|  | pINA1055/5 | 79.7% | 183.8 |
|  | pINA1055/6 | 87.1% | 194.1 |
|  | pINA1055/2 | ND | 190.7 |
|  | pINA1055/3 | ND | 165.7 |
|  |  |  | mean value = 183.0 u |

Two independent transformants were analysed in the case of pINA1053, live in the case of pINA1054 and six in the case of pINA1055. For each culture, the β-galactosidase activity was measured in duplicate.

Some of the above transformants were analyzed to determine the copy number of the replicative plasmid, in selective medium, as previously described (Fournier et al., 1991). The plasmidic and genomic DNA was extracted and digested with ClaI and SalI restriction enzymes, generating a LEU2-carrying DNA fragment of 7.8 Kb from the plasmid and one of 5.3 Kb from the genome. These samples were analyzed by Southern blotting, using a 32P-labelled LEU2 promoter probe (data not shown). "Adobe Fotoshop" and "NIH Image" softwares were respectively used to scan and to quantify the autoradiography. The ratio of labelling in the plasmidic LEU2 band to that in the genomic LEU2 band was determined (Table 10). It corresponds to the mean copy number of the replicative plasmid per cell, under selective conditions.

This mean copy number was around 0.8–0.9 in the case of pINA1053, and around 0.7–1.0 in the case of pINA1054 and 1055. It corresponds roughly to the percentage of cells carrying the replicative plasmid in selective medium (namely respectively 78%, 78–88% and 80–87% as shown in Table 9). This indicates that only one copy of pINA1053, 1054 and 1055 plasmids was present per JM23SB plasmid-containing cell.

This low copy number, expected from the centromeric contribution of ARS in Y. lipolytica (see Fournier et al., 1993) does not allow to increase the expression directed by the hybrid promoters. Nevertheless, the replicative plasmids with the optimized promoters are able to drive a strong expression in selective minimal medium, similar to that observed with the corresponding integrative vectors. They constitute a tool that can be used, in any leu2⁻ *Y. lipolytica* strain, to obtain high levels of heterologous protein.

TABLE 10

Ratio of the quantities of plasmidic to genomic LEU2-carrying DNA fragments from *Y. lipolytica* JM23SB strains transformed with the replicative plasmids carrying hybrid promoters, in selective medium.

| replicative plasmid promoter | pINA1053 minimal LEU2 prom. | pINA1054 + 4 direct "UAS1B" | pINA1055 + 4 inverted "UAS1B" |
|---|---|---|---|
| /transformant:ratio | /1:0.89 | /1:0.98 | /1:0.72 |
|  | /2:0.80 | /2:0.67 | /4:0.73 |
|  |  | /3:0.81 | /5:0.86 |
|  |  | /5:0.81 | /6:1.00 |

The DNA of two independent transformants was analysed in the case of pINA1053, of four in the case of pINA1054 and 1055. The ratio of the quantities of plasmidic to genomic LEU2-carrying DNA fragments corresponds to the ratio of the replicative plasmids to the yeasts cells, in a culture under selective conditions.

EXAMPLE 7

Replacement of the LEU2 TATA Box From Hybrid Promoters With Those of Other *Y. lipolytica* Genes Materials & Methods as in Example 1

In order to test if the LEU2 TATA box present in the hybrid promoters from pINA993 and 994 (Example 4) could be replaced without altering the properties of these plasmids, we choose to use either the TATA box of the PHO2 gene or that of the XPR2 gene itself. The following plasmids were constructed (see FIG. 10):

pINA1056: similar to pINA781 except for the TATA box and ATG region from LEU2, replaced by those from the *Y. lipolytica* PHO2 gene.

pINA1059: similar to pINA795 (one direct copy of "UAS1B") with same modification.

pINA1057: similar to pINA993 (4 direct copies of "UAS1B") with same modification.

pINA1058: similar to pINA994 (4 inverted copies of "UAS1B") with same modification.

pINA1204: similar to pINA781 except for the TATA box and ATG region from LEU2, replaced by those from the *Y. lipolytica* XPR2 gene.

pINA1207: similar to pINA795 (one direct copy of "UAS1B") with same modification.

pINA1205: similar to pINA993 (4 direct copies of "UAS1B") with same modification.

pINA1206: similar to pINA994 (4 inverted copies of "UAS1B") with same modification.

The β-galactosidase activity of JM23SB strains carrying integrated plasmids with hybrid promoters based on the PHO2 TATA box are shown in the Table 11. The *Y. lipolytica* native PHO2 promoter is induced in low phosphate media (Treton et al., 1992). However, a PHO2 promoter reduced to its proximal 260 bp (retaining the TATA box, two CT-rich boxes and a CAAT-like box) was shown to escape this regulation and to be almost constitutive, with the higher activity observed in YPD medium (Treton et al., 1992). Therefore we choose to test our constructs based on a smaller fragment of the PHO2 promoter (proximal 116 bp) only in the YPD rich medium.

The β-galactosidase activity directed by the minimal PHO2 promoter was very low. The addition of one or four copies of "UAS1B" fragment enhanced the activity, but it remained at low levels (around 8 u with four copies).

TABLE 11

β-galactosidase activity of *Y. lipolytica* JM23SB strains carrying integrated plasmids with hybrid promoters based on the PHO2TATA box, in YPD medium.

| | promoter: | | | | |
|---|---|---|---|---|---|
| | minimal PHO2 prom. | id. + 1 direct "UAS1B" | id. + 4 direct "UAS1B" | id. + 4 inverted "UAS1B" | native PHO2 prom. |
| | | | plasmid: | | |
| | pINA1056 | pINA1059 | pINA1057 | pINA1058 | p3L4/61YL |
| β-galactosidase activity (u β-gal/ml × mn × OD$_{600}$) in YPD medium. | 0.12 | 0.27 | 8.7 | 7.3 | 1.65 |

Three independent integrants were analysed for each plasmid and the β-galactosidase activity was measured in duplicate.

TABLE 12

β-galactosidase activity of *Y. lipolytica* JM23SB strains carrying integrated plasmids with hybrid promoters based on the XPR2 TATA box, in different media.

| | | β-galactosidase activity (u β-gal/ml × mn × OD$_{600}$) | | | |
|---|---|---|---|---|---|
| promoter | plasmid | inducing med. YPDm (pH 6.8) | repressing MMAm med. | YPDm (pH 4.0) | rich YPD med. |
| minimal XPR2 prom. | pINA1204 | 0.25 | 0.023 | 0.35 | 0.16 |
| id. + 1 direct "UAS1B" | pINA1207 | 9.2 | 0.22 | 32.4 | 8.9 |
| id. + 4 direct "UAS1B" | pINA1205 | 1059.4 | 134.2 | 732.7 | 681.9 |

TABLE 12-continued

β-galactosidase activity of *Y. lipolytica* JM23SB strains carrying integrated plasmids
with hybrid promoters based on the XPR2 TATA box, in different media.

| | | β-galactosidase activity (u β-gal/ml × mn × OD$_{600}$) | | | |
|---|---|---|---|---|---|
| promoter | plasmid | inducing med. YPDm (pH 6.8) | repressing MMAm med. | YPDm (pH 4.0) | rich YPD med. |
| id. + 4 inverted "UAS1B" | pINA1206 | 1050.4 | 165.8 | 689.2 | 695.8 |
| XPR2 native promoter | pINA404 | 303.2 | 1.6 | 3.6 | 65.1 |

Three independent integrants were analysed for each plasmid and the β-galaclosidase activity was measured in duplicate.

In order to compare our results with those obtained with the native PHO2 promoter, we measured the b-galactosidase activity of the p3L4/61YL plasmid, carrying a translational fusion of the PHO2 promoter to the lacZ gene (Treton et al., 1992 and FIG. 10). This plasmid was integrated into the genome of JM12 (Treton et al., 1992), a *Y. lipolytica* strain isogenic to JM23SB (except for the absence of integrated pINA300' and for the presence of a wild-type XPR2 gene). The activity driven by the native PHO2 promoter was very low (1.65 u). Thus, the PHO2-based hybrid promoters with four UAS1B copies, although weak, were much more efficient than the native PHO2 promoter.

The β-galactosidase activity of JM23SB strains carrying integrated plasmids with hybrid promoters based on the XPR2 TATA box are shown in the Table 12. In all media tested, the activity of the minimal XPR2 promoter was very low, and was greatly enhanced by the addition of "UAS1B" fragments. The hybrid promoters with four copies of "UAS1B" were able to drive a very high level of expression in the YPDm inducing medium: 1050 u, more than threefold the level obtained with the native XPR2 promoter. This represents a 4000 fold increase compared to the level obtained with the minimal XPR2 promoter alone, in the YPDm medium. The increase was around 40 fold with the addition of a single copy of "UAS1B".

With four copies of "UAS1B", the activities in the rich YPD medium were also very high (roughly 680–690 u).

However, the levels of expression of the hybrid promoters with four copies of "UAS1B" in the repressing MMAm medium were several fold lower: roughly 150 u. In this medium, the minimal XPR2 promoter also exhibited an activity tenfold lower than in the inducing medium. Although only 12 bp upstream of the XPR2 TATA box and 58 bp between this box and the ATG were conserved (which do not present any homology to known regulatory sequences), the minimal XPR2 promoter seems to be sensitive to the repression by carbon and/or nitrogen sources. Although the addition of "UAS1B" fragments enhanced strongly the expression in repressing MMAm medium (about tenfold with one copy and up to 6000 fold with four copies), this increase was however not sufficient to promote a very high level of expression.

In YPDm(pH 4.0) medium, which normally "represses" the complete XPR2 promoter, the minimal XPR2 promoter exhibited a level of expression slighly higher than in inducing and rich media. The activity driven by the hybrid promoter with one "UAS1B" copy was threefold higher than in inducing and rich media. In contrast, the activities driven, in YPDm at pH 4.0, by the hybrid promoters with four "UAS1B" copies, although very high (690–730 u, corresponding to a 2000 fold increase), were slightly inferior to those at pH 6.8.

In conclusion, the levels of expression driven by the hybrid promoters of pINA1205 and 1206 are interesting, but 6–8 fold differences are observed between the activities in YPDm(pH 6.8) inducing and MMAm repressing media. These hybrid promoters have retained some regulating elements and, in contrast to those based on the minimal LEU2 promoter, are not constitutive.

These results show that the choice of a peculiar TATA box is very important for the properties of the resulting hybrid promoters: among those tested, only the LEU2 minimal promoter allowed the construction of strong constitutive optimized promoters.

EXAMPLE 8

Expression and Secretion of Bovine Chymosin Precursor Directed by Hybrid Promoters Unless specified, Materials & Methods as in Example 1

The hybrid promoters described in the Example 4 were used to express the prorennin A allele, encoding bovine chymosin, a protein widely used in food industry. This enzyme is expressed as a zymogen precursor (prochymosin or prorennin) and is autocatalytically activated at low pH, by self cleavage. It was previously shown by Franke et al. (1988) that prorennin could be expressed in *Y. lipolytica* and efficiently secreted in the culture medium, using the secretion signals of the XPR2 gene. In contrast to the situation in *S. cerevisiae*, no residual chymosin activity was found within the cells (Franke et al., 1988; Nicaud et al., 1991). The prorennin secreted in *Y. lipolytica* cultures was not glycosylated, although the amino acid sequence of the gene included two tripeptide putative glycosylation signals (see EP 220 864). We constructed vectors carrying a translational fusion of the hybrid promoters from pINA781 (minimal LEU2 promoter), pINA993 (same plus four direct copies of "UAS1B") and pINA994 (same plus four inverted copies of "UAS1B") with the prepro region (alkaline protease secretion signal: 157 amino acids) of XPR2 gene followed by the prorennin A allele cDNA sequence. These later elements were obtained from the pLX-34 plasmid (described in EP 220 864) and used to construct the following plasmids, as described in the FIGS. 11A–C:

pINA1208 (promoter from pINA781: XPR2 prepro region: prorennin)

pINA1209 (promoter from pINA993: XPR2 prepro region: prorennin)

pINA1210 (promoter from pINA994: XPR2 prepro region: prorennin)

In order to compare our results to those obtained with the native XPR2 promoter, we constructed pINA1214 plasmid, similar to the above vectors but containing the XPR2 promoter from pINA354 instead of the hybrid promoters. This plasmid was obtained in a three fragment ligation involving:

the 6650 bp NotI-partial SauI DNA fragment from pINA1208, carrying pBR322 sequence, LEU2 gene and the downstream part of the XPR2 prepro region, fused to the prorennin gene (see FIG. 11C).

the 2618 bp NotI-ApaI DNA fragment from pINA354 (see FIG. 4), carrying the upstream part of the XPR2 promoter.

a 148 bp ApaI-SauI DNA fragment, issued from the digestion of a 568 bp PCR fragment, synthesized using pINA303 (see FIG. 5) as a matrix and the two oligonucleotides "LB" and "XPR" (described respectively in the commentaries to the FIGS. 3 and 11B). The digested fragment contains the downstream part of the XPR2 promoter and the upstream part of the XPR2 prepro region.

pINA1214 contains the native XPR2 promoter and prepro region; the translational fusion to the prepro region and the prorennin gene is the same as in pINA1208 to 1210 (shown in FIG. 11C). The above constructs were used to transform activated in the presence of 0.25 N HCl (pH 2) for 1 h at 25° C. To 100 μl of activated supernatant, and serial twofold dilutions in the same medium, were added 100 μl of skim milk (Difco, 12% in 42 mM sodium acetate, 14 mM calcium chloride, pH 6.3) and the microtitration plaques were incubated at 37° C. for 15 mn in the case of YPD and 2 h in the case of MMAm culture supernatants. The prorennin standard was purchased from Sigma. A 10 mg/l solution in YPD or MMAm medium was activated as above; 100 μl and serial twofold dilutions in the same medium were tested in parallel to the activated supernatants, in order to allow the quantification of chymosin activity. During the titration of the MMAm samples, 100 μg/ml of purified acetylated BSA were added in order to prevent rennin adsorption on the microtitration plaque and to stabilize its activity.

The results are shown in the Table 13.

TABLE 13 secreted chymosin activity, measured in the activated culture supernatants, of *Y. lipolytica* JM23SB strains carrying integrated plasmids with different promoters, grown at 23° C. in rich YPD or minimal MMAm medium.

rich YPD medium

| | | | secreted prorennin in mg/l | | | |
|---|---|---|---|---|---|---|
| promoter | plasmid | culture time | 24 h | 32 h | 40 h | 48 h |
| minimal LEU2 prom. | pINA1208 | | U (<0.70) | U (<0.31) | ND | U (<0.31) |
| id. + 4 direct "UAS1B" | pINA1209 | | 3.5 | 3.87 | ND | 0.62 |
| id. + 4 inverted "UAS1B" | pINA1210 | | 3.25 | 4.70 | 7.50 | 2.58 |
| XPR2 native promoter | pINA1214 | | 1.72 | 1.25 | 2.50 | 1.25 |
| LEU2 native promoter | pLX-34 | | U (<0.47) | 0.62 | U (<1.87) | U (<0.70) | minimal MMAm medium

| | | secreted prorennin in mg/l | | | | | |
|---|---|---|---|---|---|---|---|
| promoter | plasmid | 24 h | 32 h | 40 h | 48 h | 62 h | 72 h |
| minimal LEU2 prom. | pINA1208 | U (<1.25) | U (<1.25) | ND | U (<0.94) | U (<1.87) | ND |
| id. + 4 direct "UAS1B" | pINA1209 | 4.0 | 4.20 | ND | ND | 4.50 | 4.0 |
| id. + 4 inverted "UAS1B" | pINA1210 | 4.6 | 4.25 | 7.50 | 10.0 | 4.50 | 4.0 |
| XPR2 native promoter | pINA1214 | U (<1.25) | ND | U (<1.90) | U (<1.25) | U (<1.87) | ND |
| LEU2 native promoter | pLX-34 | U (<1.25) | ND | 3.75 | 5.0 | U (<1.87) | U (<2.0) |

Measures were performed, at least in duplicate, on two independent integrants in the case of pINA1208, three in the cases of pINA1209, 1214 and pLX-34, and four in the case of pINA1210.
"U" stands for "undetectable": the integrants gave the same effect that activated culture medium alone; the limit of detection in each test is indicated betwen brackets.

*Yarrowia lipolytica* JM23SB strain (integration at the pBR platform, directed by NotI digestion).

In order to compare our results to those obtained with the native LEU2 promoter, we used the pLX-34 plasmid (EP 220 864 and FIG. 11A). The integration of this vector into JM23SB genome, at the pBR platform, was directed by NdeI dgestion (since NotI site is absent from the pBR sequence of pLX-34).

The culture supernatants of several transformants were assayed for milk clotting activity according to a modification of the method of Franke et al. (1988). Briefly, the assay consisted in determining, in microtitration plaques, which dilution of activated culture supernatants retained enough rennin activity to clot buffered skim milk, in a given time. The results were compared with those obtained with dilutions of a purified rennin standard. The cultures were performed in YPD medium for 24 to 48 h, or in MMAm medium for 24 to 72 h, at 23° C. The supernatants were The secreted rennin activity driven by the hybrid promoter of pINA1210 (4 inverted "UAS1B" copies) was high: around 7.5 mg/l after 40 h of culture in YPD and 10 mg/l after 48 h of culture in MMAm medium. The $OD_{600}$ attained in these media during the stationary phase being respectively around 20 and around 12, the secreted rennin activity per OD unit driven by pINA1210 was 0.37 mg/l×$OD_{600}$ in YPD medium and 0.83 mg/l×$OD_{600}$ in MMAm medium. The activity driven by the hybrid promoter of pINA1209 (4 direct "UAS1B" copies) was similar for the different culture times tested, in both media.

The secreted rennin activity decreased after long culture times (between 40 and 48 h in YPD medium, and between 48 and 62 h in MMAm medium), suggesting partial degradation of prorennin, maybe due to leakage of endocellular proteolytic activity.

After 32 h of culture in YPD, the activity driven by the optimized promoters (pINA1209 and 1210) was more than twelvefold higher than that from the minimal LEU2 promoter (the activity of pINA1208 remained undetectable for all culture times), threefold higher than that from the native XPR2 promoter (pINA1214) and sixfold higher than that from the native LEU2 promoter (pLX-34). After 48 h in MMAm, the activity driven by the hybrid promoter of pINA1210 was more than tenfold higher than that from the minimal LEU2 promoter (undetectable for all culture times), more than eightfold higher than that from the native XPR2 promoter (also undetectable for all culture times) and two-fold higher than that from the native LEU2 promoter.

The measured rennin activities driven by the hybrid promoters and by the native XPR2 promoter were not higher in YPD than in MMAm medium, contrary to our previous observations with the β-galactosidase activities (see Example 4). This result could possibly be due to an artefactual underestimation of the rennin activity in YPD medium: indeed, the *Y. lipolytica* strain used, JM23SB, carries a wild type AXP gene (coding for the acid extracellular protease). This protease was shown to be partially active at pH 6 (approximate pH of the unbuffered YPD medium), retaining roughly ¼ of its maximum activity (at pH 4), whereas the activity at pH 6.8 was negligible (Yamada and Ogrydziak, 1983). The AXP gene was recently shown to be expressed at pH 6 (Cordero-Otero and Gaillardin, 1996). This protease could therefore contribute to lower the level of rennin activity measured in the YPD medium: the activity would probably be higher in a strain carrying an inactivated AXP gene.

We wish to emphasize that only a limited number of culture conditions were tested, and that the levels reported here would probably be significantly enhanced by optimizing the conditions of culture and the genetic background of the producing strain.

The culture supernatants from JM23SB and from some of the integrants (carrying pINA1208, 1210, 1214 or pLX-34) were analyzed by Western blotting. The supernatants from 10 ml cultures, grown at 28° C., for 40 h in YPD medium or 48 h in MMAm medium, were precipitated with trichloracetic acid and loaded on denaturing acrylamide gels, as previously described (Sambrook et al., 1989). Similarly, 1 ml of supernatant from 48 h or 62 h cultures, grown in MMAm at 23° C., was concentrated by lyophilisation, and loaded on denaturing acrylamide gels. After electrophoresis, the gels were transferred to a nitrocellulose membrane (as described in Sambrook et al., 1989) and the Western blots were revealed by incubation with, first, a polyclonal rabbit antibody raised against rennin (provided by C. Strick, Pfizer Co), and then, a goat anti-rabbit IgG conjugated to alkaline phosphatase (purchased from Promega and used according to specifications of the supplier).

For both TCA-precipitated and lyophilised samples, a single band of approximately 40 kD, co-migrating with the prorennin standard control, was observed for the integrants carrying pINA1210 (hybrid promoter with four inverted "UAS1B" copies), grown in YPD or MMAm medium (data not shown). It was also observed for the integrant carrying pINA1214 (native XPR2 promoter), when grown in YPD medium, but not when grown in MMAm medium. In contrast, this band was undetectable in samples from JM23SB strain and from integrants carrying pINA1208 (minimal LEU2 promoter) and pLX-34 (native LEU2 promoter), in both YPD and MMAm media.

Our results demonstrate that *Y. lipolytica* integrants carrying the optimized promoters based on "UAS1B" fragment are able to drive a strong quasi-constitutive expression and an efficient secretion of the prorennin A. The results obtained with these promoters are clearly better than those of the previously used XPR2 and LEU2 promoters, in both rich and minimal media.

Legend for FIG. 3.

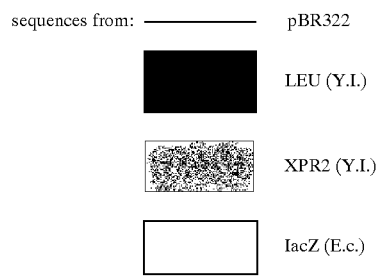

BIBLIOGRAPHY

Ahearn D G, Meyers S P, Nichols R A (1968) Appl Microbiol 16: 1370–1374.
Bassel J, Mortimer R (1973) J Bacteriol 114: 894–896.
Blanchin-Roland S, Cordero Otero R R, Gaillardin C (1994) Mol Cell Biol 14: 327–338.
Cordero-Otero R, Gaillardin C (1996) submitted
Davidow L S, Apostolakos D, O'Donnell M M, Proctor A A, Ogrydziak D M, Wing R A, Stasko I, De Zeeuw J R (1985) Curr Genet 10: 39–48.
Davidow L S, O'Donnell M M, Kaczmarek F S, Pereira D A, De Zeeuw J R, Franke A E (1987) J Bacteriol 169: 4621–4629.
Fournier Ph, Guyaneux, L, Chasles M, Gaillardin C (1991) Yeast 7: 25–36
Fournier Ph, Abbas A, Chasles M, Kudla B, Ogrydziak D M, Yaver D, Xuan J W, Peito A, Ribet A M, Feynerol C, He F, Gaillardin C (1993) Proc Natl Acad Sc 90: 4912–4916
Franke A E, Kaczmarek F S, Eisenhard M E, Geoghegan K F, Danley D E, De Zeeuw J R, O'Donnell M M, Gollaher M G, Lance S D (1988) Dev Ind Microbiol 29: 43–57
Gaillardin C, Ribet, A M (1987) Curr Genet 11: 369–375.
Gutz H, Heslot H, Leupold U, Loprieno N (1974) Handbook of genetics, ed King R C, Plenum Press, NY, vol. 1: 395–446
Hoffman C S, Winston F (1987) Gene 57: 267–272
Kamada M, Ogura S, Oda K, Murao S (1972) Agric Biol Chem 36: 171–175.
Klug M J, Markovetz A J (1967) J Bacteriol 93: 1847–1851.
Klug M J, Markovetz A J (1969) Biotech Bioeng 11: 427–440.
Matoba S, Fukayama J, Wing R, Ogrydziak D M (1988) Mol Cell Biol 8: 4904–4916.
Miller J H (1972) Cold Spring Harbor Lab Press, Cold Spring Harbor, N.Y., 352–355.
Nicaud J M, Fabre E, Beckerich J M, Fournier P. Gaillardin G (1989) J Biotechnol 12: 285–292.
Nicaud J M, Fournier Ph, La Bonnardière C, Chasles M, Gaillardin C (1991) J Biotech 19: 259–270
Ogrydziak D M, Demain A L, Tannenbaum S R (1977) Biochem Biophys Acta 497: 525–538.
Ogrydziak D M, Scharf S J (1982) J Gen Microbiol 128: 1225–1234.
Raleigh E A, Lech K, Brent R (1989) in Curr Protoc Mol Biol, eds Ausubel F M et al., Publishing Associates and Wiley Interscience, NY, Unit 1.4
Sambrook J, Fritsch E F, Maniatis T (1989) Molecular cloning: a laboratory manual, 2nd ed. Cold Spring Harbor Lab Press, Cold Spring Harbor, N.Y.
Tobe S T, Takami S, Ikeda S, Mitsugi K (1976) Agr Biol Chem 40: 1037–1092.
Treton B Y, Le Dall M T, Gaillardin C (1992) Curr Genet 22: 345–355
Yamada T, Ogrydziak D M (1983) J Bacter 154 (n° 1): 23–31
Yanish-Perron C, Viera J, Messing J (1985) Gene 33: 103–199
Yon J, Fried M (1989) Nuc Acids Res 17: 4895

What is claimed is:

1. An isolated upstream activating sequence functional in Yarrowia consisting essentially of either at least two copies of at least one sequence of or at least one copy of at least two sequences or functional fragments thereof, wherein said sequences are selected from the group consisting of:
   a) SEQ. ID NO:1 or a sequence possessing at least 80% identity to SEQ. ID NO:1;
   b)
      i) SEQ. ID NO:1 or a sequence possessing at least 80% identity to SEQ. ID NO:1 and
      ii) at least one copy of SEQ. ID NO:2, or a sequence possessing at least 80% identity to SEQ. ID NO:2;
   c)
      i) SEQ. ID NO:1 or a sequence possessing at least 80% identity to SEQ. ID NO:1 and
      ii) at least one copy of SEQ. ID NO:3, or a sequence possessing at least 80% identity to SEQ. ID NO:3; and
   d) SEQ. ID NO:4 or a sequence possessing at least 80% identity to SEQ. ID NO:4.

2. The upstream activating sequence according to claim 1 consisting essentially of two copies of either a) or b).

3. The upstream activating sequence according to claim 1 consisting essentially of two copies of c).

4. The upstream activating sequence according to claim 1 consisting essentially of two copies of d).

5. The upstream activating sequence according to claim 1, wherein the total number of copies of said sequences a), b), c) or d) is in the range of 2 to 8 and the number of copies of SEQ. ID NO. 2 is in the range of 0 to 16.

6. The upstream activating sequence according to claim 1, consisting essentially of three tandem copies of a sequence selected from a) b), c) or d).

7. The upstream activating sequence according to claim 1, consisting essentially of four tandem copies of a sequence selected from a), b), c) or d).

8. A promoter sequence functional in Yarrowia, comprising an upstream activating sequence according to claim 1.

9. A promoter sequence according to claim 8 which is functional in *Yarrowia lipolytica*.

10. A promoter sequence according to claim 8, characterized in that the TATA box is that of a *Yarrowia lipolytica* gene promoter.

11. A promoter sequence according to claim 8, characterized in that the TATA box is that of a gene differing from the XPR2 gene.

12. A vector for the expression of a protein in yeast, comprising a promoter sequence according to claim 8, operably linked to a gene of interest wherein said gene encodes a protein of interest.

13. The vector according to claim 12, wherein the gene of interest encodes a heterologous protein.

14. The vector according to claim 13, wherein the yeast is *Yarrowia lipolytica*.

15. The vector according to claim 14, further comprising sequences allowing its insertion into the chromosome of said *Yarrowia lipolytica*.

16. The vector according to claim 14, further comprising a sequence allowing the vector to replicate autonomously as an episome in *Yarrowia lipolytica*.

17. A recombinant Yarrowia genome, comprising a vector according to claim 15, wherein several copies of said vector are inserted into the chromosome of said *Yarrowia lipolytica*.

18. A recombinant yeast, wherein said yeast is *Yarrowia lipolytica* transformed with a vector according to claim 16.

19. A recombinant yeast according to claim 18, wherein the promoter sequence operably linked to the gene of interest is integrated into the chromosome of said yeast, in at least one copy.

20. A recombinant yeast according to claim 18, wherein the vector is present as an autonomously replicating episome in said *Yarrowia lipolytica*.

21. A process for producing a protein in *Yarrowia lipolytica*, comprising the step of culturing recombinant *Yarrowia lipolytica* cells according to claim 20.

22. A process for producing an heterologous protein comprising the steps of:
   i) introducing into a *Yarrowia lipolytica* a vector according to claim 12,
   ii) culturing said *Yarrowia lipolytica* obtained in step i) in a medium substantially devoid of peptones, and
   iii) recovering said heterologous protein.

23. A process for enhancing the expression of a protein in *Yarrowia lipolytica*, comprising the step of introducing in said *Yarrowia lipolytica* a promoter sequence operably linked to a gene of interest, said promoter sequence comprising either at least two copies of at least one sequence or at least one copy of at least two sequences or functional fragments thereof, wherein said sequences are selected from the group consisting of:
   a) SEQ. ID NO:1 or a sequence possessing at least 80% identity to SEQ. ID NO:1;
   b)
      i) SEQ. ID NO:1 or a sequence possessing at least 80% identity to SEQ. ID NO:1 and
      ii) at least one copy of SEQ. ID NO:2, or a sequence possessing at least 80% identity to SEQ. ID NO:2;
   c)
      i) SEQ. ID NO:1 or a sequence possessing at least 80% identity to SEQ. ID NO:1 and
      ii) at least one copy of SEQ. ID NO:3, or a sequence possessing at least 80% identity to SEQ. ID NO:3; and
   d) SEQ. ID NO:4 or a sequence possessing at least 80% identity to SEQ. ID NO:4.

24. A recombinant yeast, wherein said yeast is *Yarrowia lipolytica* transformed with a vector according to claim 12.

25. A recombinant yeast, wherein said yeast is *Yarrowia lipolytica* transformed with a vector according to claim 13.

26. A recombinant yeast, wherein said yeast is *Yarrowia lipolytica* transformed with a vector according to claim 14.

27. A recombinant yeast, wherein said yeast is *Yarrowia lipolytica* transformed with a vector according to claim 15.

28. An isolated upstream activating sequence functional in Yarrowia comprising either at least two copies of at least one sequence or at least one copy of at least two sequences or functional fragments thereof, wherein said sequences are selected from the group consisting of:
   a) SEQ. ID NO:1 or a sequence possessing at least 80% identity to SEQ. ID NO:1;
   b)
      i) SEQ. ID NO:1 or a sequence possessing at least 80% identity to SEQ. ID NO:1 and
      ii) at least one copy of SEQ. ID NO:2, or a sequence possessing at least 80% identity to SEQ. ID NO:2;
   c)
      i) SEQ. ID NO:1 or a sequence possessing at least 80% identity to SEQ. ID NO:1 and
      ii) at least one copy of SEQ. ID NO:3, or a sequence possessing at least 80% identity to SEQ. ID NO:3; and
   d) SEQ. ID NO:4 or a sequence possessing at least 80% identity to SEQ. ID NO:4.

* * * * *

UNITED STATES PATENT AND TRADEMARK OFFICE
CERTIFICATE OF CORRECTION

PATENT NO. : 6,083,717
DATED : July 4, 2000
INVENTOR(S) : Catherine Madzak, et al.

It is certified that error appears in the above-identified patent and that said Letters Patent is hereby corrected as shown below:

Column 35,
Line 41, Claim 1 after "sequence" delete "of".

Signed and Sealed this

Twenty fifth Day of September, 2001

Attest:

*Attesting Officer*

NICHOLAS P. GODICI
*Acting Director of the United States Patent and Trademark Office*